United States Patent [19]

Nakashima et al.

[11] Patent Number: 5,641,430
[45] Date of Patent: Jun. 24, 1997

[54] SILACYCLOHEXANE COMPOUNDS, PREPARATION THEREOF, LIQUID CRYSTAL COMPOSITIONS COMPRISING THE SAME, AND LIQUID CRYSTAL DEVICES COMPRISING THE COMPOSITIONS

[75] Inventors: Mutsuo Nakashima; Takaaki Shimizu; Tsutomu Ogihara; Takeshi Kinsho; Tatsushi Kaneko; Kazuyuki Asakura, all of Niigata-ken; Hideshi Kurihara, Kawasaki, all of Japan

[73] Assignee: Shin-Etsu Chemical Co., Ltd., Tokyo, Japan

[21] Appl. No.: 566,392

[22] Filed: Dec. 1, 1995

[30] Foreign Application Priority Data

Dec. 2, 1994 [JP] Japan ..................... 6-329310
Feb. 2, 1995 [JP] Japan ..................... 7-037558

[51] Int. Cl.$^6$ .................... C09K 19/34; C09K 19/30; C07F 7/08
[52] U.S. Cl. ............... 252/299.61; 556/406; 252/299.63
[58] Field of Search .................. 252/299.61; 556/406

[56] References Cited

U.S. PATENT DOCUMENTS 5,454,977  10/1995  Shimizu et al. ............... 252/299.61

FOREIGN PATENT DOCUMENTS

| 0657460 | 6/1995 | European Pat. Off. . |
| 0665232 | 8/1995 | European Pat. Off. . |
| 63-2246 | 1/1988 | Japan . |
| 63-46740 | 9/1988 | Japan . |
| 6013731 | 9/1992 | Japan . |
| 6123208 | 11/1995 | Japan . |

*Primary Examiner*—C. H. Kelly
*Attorney, Agent, or Firm*—Lowe, Price, LeBlanc & Becker

[57] ABSTRACT

A silacyclohexane compound of the following formula (I) or (II)

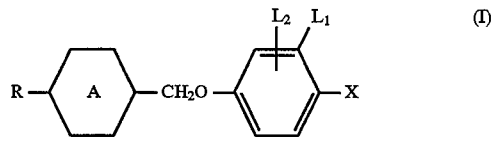

wherein R is an organic residue,

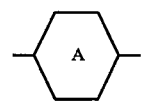

represents an unsubstituted or substituted trans-1-sila-1,4-cyclohexylene group or trans-4-sila-1,4-cyclohexylene group, $L_1$ and $L_2$ independently represent H, F, Cl or $CH_3$; and X represents an organic residue, CN, F or Cl, or

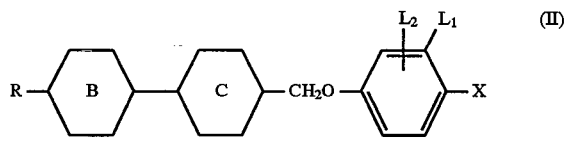

wherein R, $L_1$, $L_2$ and X are, respectively, as defined above, and at least one of

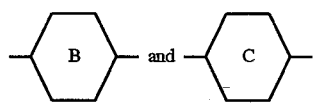

represents an unsubstituted or substituted trans-1-sila-1,4-cyclohexylene group or trans-4-sila-1,4-cyclohexylene group, and the other may be a trans-1,4-cyclohexylene group. The preparation of these compounds is described along with a composition comprising the compound (I) and/or (II) and a display device comprising the composition.

23 Claims, No Drawings

SILACYCLOHEXANE COMPOUNDS, PREPARATION THEREOF, LIQUID CRYSTAL COMPOSITIONS COMPRISING THE SAME, AND LIQUID CRYSTAL DEVICES COMPRISING THE COMPOSITIONS

BACKGROUND OF THE INVENTION

1. Field of the Invention

This invention relates to novel silacyclohexane compounds and the preparation thereof. The invention also relates to liquid crystal compositions comprising the silacyclohexane compound or compounds and to devices comprising the compositions.

2. Description of the Prior Art

The liquid crystal display devices utilize optical anisotropy and dielectric anisotropy of liquid crystal substances. Depending on the mode of display, different types of display systems are known including those of a twisted nematic type (TN type), a supertwisted nematic type (STN type), a super birefringence type (SBE type), a dynamic scattering type (DS type), a guest/host type, a type of deformation of aligned phase (DAP type), a polymer dispersion type (PD type), and an optical mode interference type (OMI type). The most popular display device is one which is based on the Schadt-Helfrich effect and has a twisted nematic structure.

Although the properties of the liquid crystal substances used in these liquid crystal devices depend, more or less, on the type of display, it is commonly required that the liquid crystal substances have a wide range of temperatures working as a liquid crystal and that they be stable against moisture, air, light, heat, electric field and the like. Moreover, the liquid crystal substances should desirably be low in viscosity and should ensure a short address time, a low threshold voltage and a high contrast in cells.

Liquid substances which can satisfy all the requirements have never been known when used singly. In practice, several to ten and several liquid compounds and/or latent liquid crystal compounds are used in the form of a mixture. To this end, it is important that constituent components be readily compatible with one another.

Liquid crystal substances usable as these constituent components can be broadly classified into the following groups depending on the function thereof.

(1) Compounds contributing to the reduction of viscosity and lowering of melting point of mixed liquid crystal compositions.

(2) Compounds mainly controlling electrooptic functions of liquid crystal compositions.

(3) Compounds contributing to the increase in transparency of mixed liquid crystal compositions.

(4) Compounds contributing to the control of anisotropy in refractive index of mixed liquid crystal compositions.

(5) Compounds controlling the color display and alignment of mixed liquid crystal compositions.

The compounds classified as (1) above are known including those compounds having a cyclohexane ring-methylene-oxy-benzene ring structure of the following formula having an ether bond

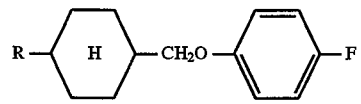

wherein R represents an alkyl group having from 1 to 8 carbon atoms as set out in Japanese Patent Publication No, 4-60976.

Moreover, those compounds having cyclohexane ring-methylene-oxy-benzene ring structured of the following formulas having an ether bond are known as having a relative high melting point or $T_{NI}$ (nematic-isotropic phase transition temperature) and a wide temperature range wherein the nematic phase is maintained

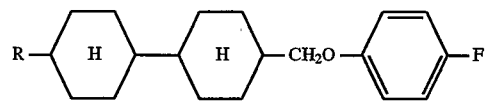

wherein R represents an alkyl group having from 1 to 10 carbon atoms as set out in Japanese Patent Publication No. 63-2246.

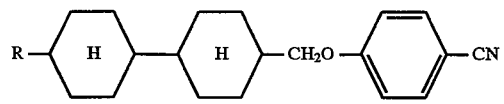

wherein R is an alkyl group having from 1 to 10 carbon atoms as set out in Japanese Patent Publication No. 63-46740.

As the liquid crystal display devices recently have wider utility, the characteristic properties required for the liquid crystal materials become severer. Especially, it is strongly required in the field of portable devices for multi media that batteries be small in size and thus, the power consumption be low. Hence, liquid crystals capable of driving at low voltage are correspondingly required. To realize the low drive potential, liquid crystal materials should have a great dielectric anisotropy ($\Delta\epsilon$).

On the other hand, as liquid crystal display devices have wider utility in various fields, the characteristic properties required for liquid crystal materials become severer. In fact, liquid crystal materials now demanded should have an improved low temperature performance, a wider working temperature satisfying on-vehicle needs and a lower drive voltage on comparison with existing liquid crystal materials or compositions.

SUMMARY OF THE INVENTION

It is accordingly an object of the invent/on to provide a novel compound which has an Si-containing silacyclohexane ring in the molecule and serves as a liquid crystal substance whereby the dielectric anisotropy ($\Delta\epsilon$) is widely changeable and the compound is suitable for driving display devices at low voltage.

It is another object of the invention to provide a novel compound having an Si-containing silacyclohexane compound which is effective in reducing the viscosity and lowering the melting point of liquid crystal compositions on addition to the compositions.

It is a further object of the invention to provide a liquid crystal composition which comprise at least a compound of the type as set out above and also a liquid crystal display device comprising the composition.

The above objects can be achieved, according to one embodiment of the invention, by a silacyclohexane compound selected from the group consisting of compounds of the following formulas (I) and (II)

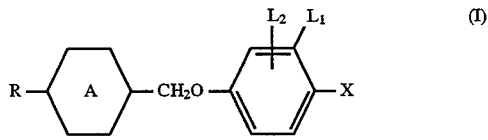

wherein R represents a linear alkyl group having from 1 to 10 carbon atoms, a branched alkyl group having from 3 to 8 carbon atom, an alkoxyalkyl group having from 2 to 7 carbon atoms, a mono or difluoroalkyl group having from 1 to 10 carbon atoms, or an alkenyl group having from 2 to 8 carbon atoms;

represents a trans-1-sila-1,4-cyclohexylene group or trans-4-sila-1,4-cyclohexylene group in which the silicon atom at the 1 or 4 position has a substituent of H, F, Cl or $CH_3$; $L_1$ and $L_2$ independently represent H, F, Cl or $CH_3$; and X represents a linear alkoxy group having from 1 to 10 carbon atoms, a linear alkoxy group having from 1 to 10 carbon atoms, an alkoxyalkyl group having from 2 to 7 carbon atoms, a mono or difluoroalkyl group having from 1 to 10 carbon atoms, an alkenyl group having from 2 to 8 carbon atoms, CN, F, Cl, $CF_3$, $CF_2Cl$, $CHFCl$, $OCF_3$, $OCF_2Cl$, $OCHFCl$, $OCHF_2$, $(O)_lCY{=}CX_1X_2$ wherein l is 0 or 1, Y and $X_1$ independently represent H, F or Cl, $X_2$ represents F or Cl, or $(O)q(C_nF_mH_{2n-m})X_3$ wherein q is 0 or 1, n is 2, 3 or 4, m is 0 or an integer of 1 to 2n, and $X_3$ represents H, F or Cl, and

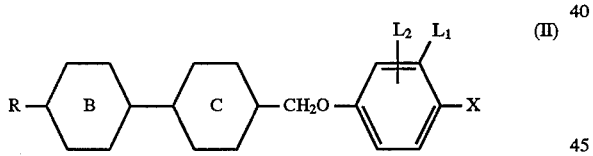

wherein R, $L_1$, $L_2$ and X are, respectively, as defined in the formula (I), and

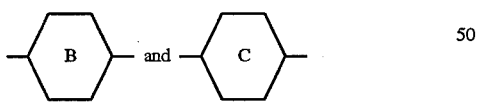

represents a trans-1-sila-1,4-cyclohexylene group or trans-4-sila-1,4-cyclohexylene group in which the silicon atom at the 1 or 4 position has a substituent of H, F, Cl or $CH_3$, and the other represents a trans-1,4-cyclohexylene group, or such a trans-1-sila-1,4-cyclohexylene group or trans-4-sila-1,4-cyclohexylene group as defined above. As will be apparent from the definition of

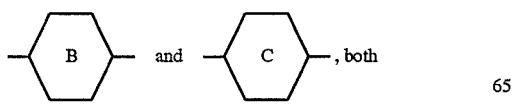

may independently be the trans-1-sila-1,4-cyclohexylene group or the trans-4-sila-1,4-cyclohexylene group as defined above, or one of them may be the trans-1-sila-1,4-cyclohexylene group or trans-4-sila-1,4-cyclohexylene group and the other may be a trans-1,4-cyclohexylne group.

The compound of the formula (I) can be prepared by a process which comprises:

reacting an organometallic compound of the general formula, R-M, wherein R is as defined in the formula (I) and M represents Li, MgP or ZnP wherein P represents a halogen atom, preferably Cl, Br or I, with a compound of the following general formula (1)

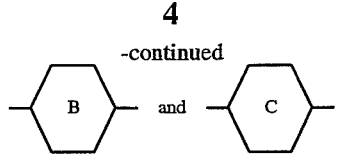

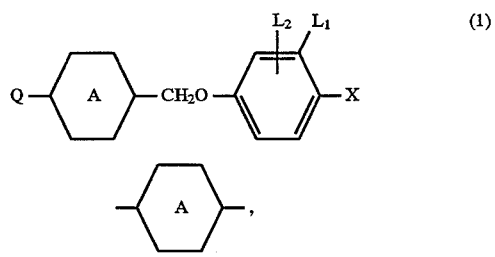

$L_1$, $L_2$ and X are, respectively, as defined in the formula (I), and Q represents a halogen atom, an alkoxy group having from 1 to 4 carbon atoms, a methanesulfonyloxy group, a benzenesulfonyloxy group, a p-toluensulfonyloxy group or a trifluoromethanesulfonyloxy group, whereby R in the organometallic compound is bonded to the carbon or silicon atom of the compound of formula (1) to obtain the compound of the general formula (I).

Alternatively, the compound of the formula (I) may be prepared by another process which comprises:

reacting a phenolic compound of fie following general formula (2)

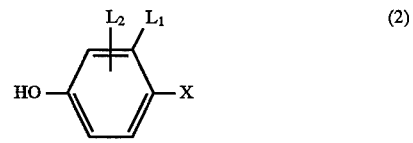

wherein $L_1$, $L_2$ and X are, respectively, as defined hereinabove, with a compound of the following general formula (3)

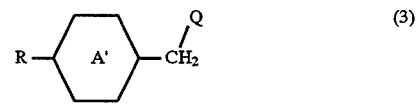

wherein

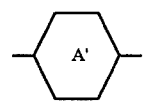

represents a trans-1-sila-1,4-cyclohexylene group or trans-4-sila-1,4-cyclohexylene group in which the silicon atom at the 1 or 4 position has a methyl group or Ar, wherein Ar represents phenyl or tolyl, R and Q are, respectively, as defined hereinabove, in the presence of a base to obtain a compound of the general formula (I) although a methyl group or Ar is attached to the silicon atom at the 1 or 4 position.

If the silacyclohexane compound obtained by this process has a moiety having the following a structural formula, i.e. Ar is attached to the silicon atom at the 1 or 4 position,

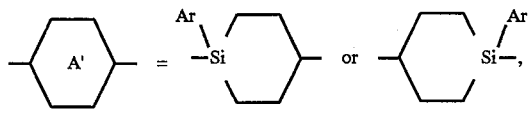

this compound is de-silylated with iodine monochloride to provide a moiety of the following formula

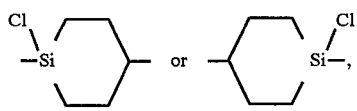

followed by reduction to convert into the moiety of the following formula

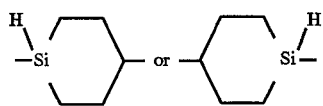

thereby obtaining a hydrosilacyclohexane compound of the general formula (I) wherein the substituent of the trans-1-sila-1,4-cyclohexylene group or trans-4-sila-1,4-cyclohexylene group is converted to hydrogen.

Furthermore, the compound of the general formula (II) can be prepared by a process which comprises:

reacting an organometallic compound of the general formula, R-M, wherein R is as defined in the formula (I) and M represents Li, MgP or ZnP wherein P is a halogen atom, preferably Cl, Br or I, with a compound of the following general formula (4)

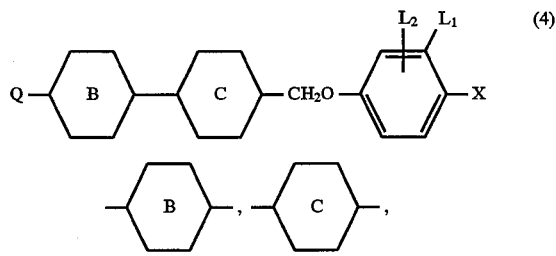

$L_1$, $L_2$ and X are, respectively, as defined in the formula (II), and Q is as defined in the formula (1), whereby R in the organometallic compound is bonded to the carbon or silicon atom of the compound of the formula (4) to obtain the compound of the general formula (II).

The compound of the formula (II) may also be prepared through carbon-carbon bonding reaction or carbon-silicon bonding reaction between an organometallic reagent of the following general formula (5)

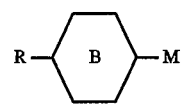

wherein R and M are, respectively, as defined above, and a compound of the following general formula (6)

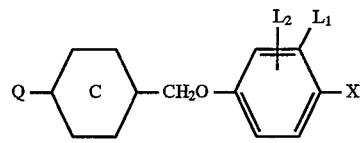

thereby obtaining a silacyclohexane compound of the general formula (II).

Like the preparation of the compound of the formula (I), the compound of the formula (II) may be prepared by a further process which comprises:

reacting a phenolic compound of the following general formula (7)

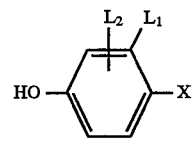

wherein $L_1$, $L_2$ and X are, respectively, as defined hereinabove, with a compound of the following general formula (8)

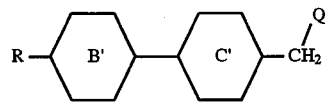

wherein R and Q are, respectively, as defined hereinabove, and one of

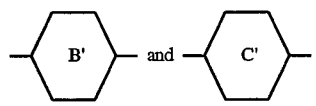

is a trans-1-sila-1,4-cyclohexylene group or trans-4-sila-1,4-cyclohexylene group wherein Si at the 1 or 4 position is substituted with a methyl group or Ar wherein Ar is phenyl or tolyl, and the other is a trans-1-sila-1,4-cyclohexylene group or trans-4-sila-1,4-cyclohexylene group substituted as defined above, or a trans-1,4-cyclohexylene group, in the presence of a base to obtain a compound of the general formula (II) wherein the methyl group or Ar is attached to the silicon atom at the 1 or 4 position.

If the silacyclohexane, compound obtained by the above process has a moiety having a phenyl or tolyl substituent as shown below as at least one of

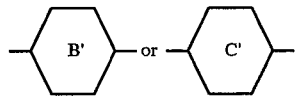

-continued

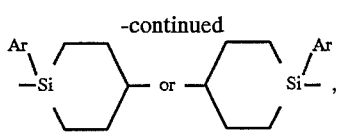

this compound is de-silylated with iodine monochloride to provide a moiety of the following formula

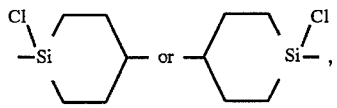

followed by reduction to convert into the moiety of the following formula

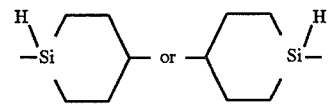

thereby obtaining a hydrosilacyclohexane compound of the general formula (II) wherein the Ar substituent of the trans-1-sila-1,4-cyclohexylene group or trans-4-sila-1,4-cyclohexylene group is converted to hydrogen.

The invention also provides a liquid crystal composition which comprises the silacyclohexane compound of the formula (I) and/or (II). Preferably, the silacyclohexane compound (I) and/or (II) is present in amounts of from 1 to 50 mole %, preferably 5 to 30 mole % of the composition. In addition, the invention provides a liquid crystal display device comprising a cell structure which comprises the liquid crystal composition mentioned above.

Among the compounds of the formula (I) according to the invention, those compounds of the formula (I), wherein X is CN, strongly tend to exhibit a tautomeric phase transition. In contrast, most of the compounds of the formula (I) wherein X is a group other than CN exhibit single phase transition or crystal-isotropic liquid phase transition, and do not exhibit appreciable electrooptic characteristics of a liquid crystal when used singly. Nevertheless, when used along with other liquid crystal substances in the form of a mixture or composition, they contribute to the reduction of viscosity and the lowering of melting point of the composition.

The compounds of both formulas (I) and (II) have the ring structure having an Si atom therein, so that when used as one of constituents of liquid crystal compositions, they can effectively reduce the viscosity of the composition and can improve a response speed along with an improvement in miscibility with other constituents at low temperatures.

Moreover, with the compounds of the formulas (I) and (II) wherein X is a substituent other than an alkyl group or an alkoxy group as defined before with respect to R, they function to lower a threshold voltage because of the great dielectric anisotropy thereof.

In general, the compounds of the formulas (I) and (II) wherein X is an alkyl or alkoxy group as mentioned above exhibit a dielectric anisotropy close to zero. Hence, it is preferred that these compounds are employed as a liquid crystal phase of display devices based on the dynamic scattering (DS) type or the type of deformation of aligned phase (DAP type). On the other hand, the compounds of the formulas (I) and (II) wherein X is a substituent other than an alkyl or alkoxy group are preferably used to prepare a liquid crystal phase having a great positive dielectric anisotropy which is employed in twisted nematic cells or in display devices based on the cholesteric-nematic phase transition.

DETAILED DESCRIPTION OF THE INVENTION

The novel compounds of the invention serving as a Liquid crystal are those of the formula (I) indicated hereinbefore. More specifically, the compounds have novel ring structures including a trans-1-silacyclohexane ring or a trans-4-silacyclohexane ring and include, for example, the compounds of the following formulas (Ia) and (Ib):

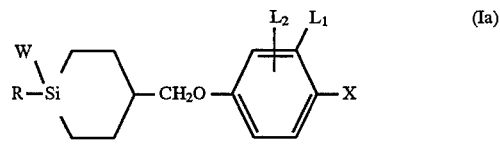

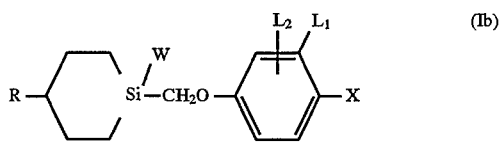

Likewise, the compounds of the formula (II) include, for example, those compounds of the following formulas (IIa) to (IIg)

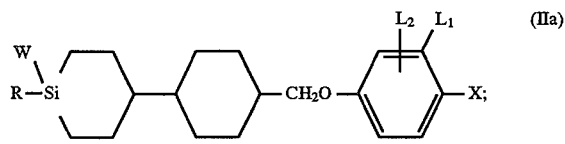

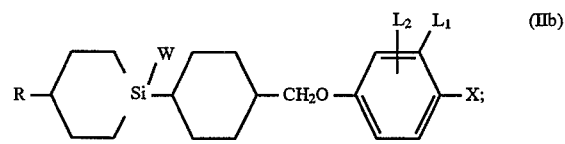

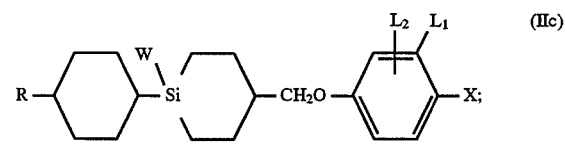

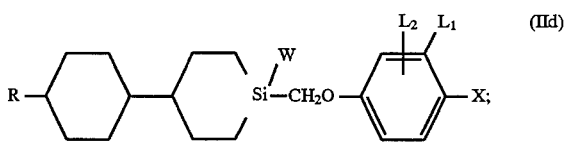

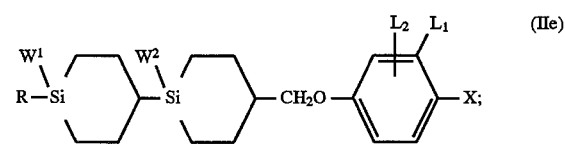

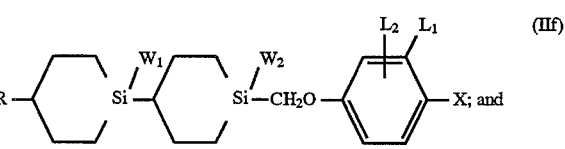

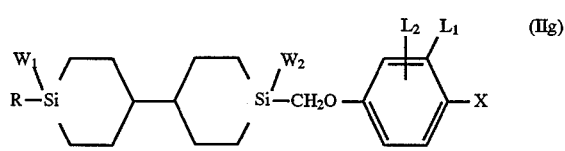

In the formulas (Ia), (Ib) and (IIa) to (IIg), R represent a linear alkyl group having from 1 to 10 carbon atoms, a branched alkyl group having from 3 to 8 carbon atoms, a mono or difluoroalkyl group having from 1 to 10 carbon atoms an alkoxyalkyl group having from 2 to 7 carbon atoms or an alkenyl group having from 2 to 8 carbon atoms, X represents a linear alkyl group having from 1 to 10 carbon atoms, a linear alkoxy group having from 1 to 10 carbon atoms, an alkoxyalkyl group having from 2 to 7 carbon atoms, a mono or difluoroalkyl group having from 1 to 10 carbon atoms, an alkenyl group having from 2 to 8 carbon atoms, CN, F, Cl, $CF_3$, $CF_2Cl$, CHFCl, $OCF_3$, $OCF_2Cl$, OCHFCl, $OCHF_2$, $(O)_lCY=CX_1X_2$ wherein l is 0 or 1, Y and $X_1$ independently represent H, F or Cl, $X_2$ represents F or Cl, or $(O)_{ti}(C_nF_mH_{2n-m})X_3$ wherein ti is 0 or 1, n is 2, 3 or 4, m is 0 or an integer of 1 to 2n, and $X_3$ represents H, F or Cl, W, $W^1$ and $W^2$ independently represent H, F, Cl or $CH_3$, and $L_1$ and $L_2$ independently represent H, F, Cl or $CH_3$.

Specific examples of the linear alkyl group having from 1 to 10 carbon and represented by R include methyl, ethyl, n-propyl, n-butyl, n-pentyl, n-hexyl, n-heptyl, n-octyl, n-nonyl and n-decyl. Specific examples of the branched alkyl group having 3 to 8 carbon atoms and represented by R include isopropyl, sec-butyl, isobutyl, 1-methylbutyl, 2-methylbutyl, 3-methylbutyl, 1-methylpentyl, 2-methylpentyl, 3-methylpentyl, 1-ethylpentyl, 1-methylhexyl, 2-methylhexyl, 3-methylhexyl, 2-ethylhexyl, 3-ethylhexyl, 1-methylheptyl, 2-methylheptyl and 3-methylheptyl. Specific examples of the alkoxyalkyl group having from 2 to 7 carbon atoms and represented by R include methoxymethyl, ethoxymethyl, propoxymethyl, butoxymethyl, pentoxymethyl, hexyloxymethyl, methoxyethyl, ethoxyethyl, propoxyethyl, butoxyethyl, pentoxyethyl, methoxypropyl, ethoxypropyl, propoxypropyl, butoxypropyl, methoxybutyl, ethoxybutyl, propoxybutyl, methoxypentyl, ethoxypentyl, and methoxyhexyl.

Specific examples of the mono or difluoroalkyl group having from 1 to 10 carbon atoms and represented by R include fluoromethyl, 1-fluoroethyl, 1-fluoropropyl, 1-fluorobutyl, 1-fluoropentyl, 1-fluorohexyl, 1-fluoroheptyl, 1-fluorooctyl, 1-fluorononyl, 1-fluorodecyl, 2-fluoroethyl, 2-fluoropropyl, 2-fluorononyl, 2-fluoropentyl, 2-fluorohexyl, 2-fluoroethyl, 2-fluorooctyl, 2-fluorononyl, 2-fluorodecyl, 3-fluoropropyl, 3-fluorobutyl, 3-fluoropentyl, 3-fluorohexyl, 3-fluoroheptyl, 3-fluorooctyl, 3-fluorononyl, 3-fluorodecyl, 4-fluorobutyl, 4-fluoropentyl, 4-fluorohexyl, 4-fluoroheptyl, 4-fluorooctyl, 4-fluorononyl, 4-fluorodecyl, 5-fluoropentyl, 5-fluorohexyl, 5-fluoroheptyl, 5-fluorooctyl, 5-fluorononyl, 5-fluorodecyl, 6-fluorohexyl, 6-fluoroheptyl, 6-fluorooctyl, 6-fluorononyl, 6-fluorodecyl, 7-fluoroethyl, 7-fluorooctyl, 7-fluorononyl, 7-fluorodecyl, 8-fluorooctyl, 8-fluorononyl, 8-fluorodecyl, 9-fluorononyl, 9-fluorodecyl, 10-fluorodecyl, difluoromethyl, 1,1-difluoroethyl, 1,1-difluoropropyl, 1,1-difluorobutyl, 1,1-difluoropentyl, 1,1-difluorohexyl, 1,1-difluoroheptyl, 1,1-difluorooctyl, 1,1-difluorononyl, 1,1-difluorodecyl, 2,2-difluoroethyl, 2,2-difluoropropyl, 2,2-difluorobutyl, 2,2-difluoropentyl, 2,2-difluorohexyl, 2,2-difluoroheptyl, 2,2-difluorooctyl, 2,2-difluorononyl, 2,2-difluorodecyl, 3,3-difluoropropyl, 3,3-difluorobutyl, 3,3-difluoropentyl, 3,3-difluorohexyl, 3,3-difluoroheptyl, 3,3-difluorooctyl, 3,3-difluorononyl, 3,3-difluorodecyl, 4,4-difluorobutyl, 4,4-difluoropentyl 4,4-difluorohexyl, 4,4-difluoroheptyl, 4,4-difluorooctyl, 4,4-difluorononyl, 4,4-difluorodecyl, 5,5-difluoroheptyl, 5,5-difluorohexyl, 5,5-difluoroheptyl, 5,5-difluorooctyl, 5,5-difluorononyl, 5,5-difluorodecyl, 6,6-difluorohexyl, 6,6-difluoroheptyl, 6,6-difluorooctyl, 6,6-difluorononyl, 6,6-difluorodecyl, 7,7-difluoroheptyl, 7,7-difluorooctyl, 7,7-difluorononyl, 7,7-difluorodecyl, 8,8-difluorooctyl, 8,8-difluorononyl, 8,8-difluorodecyl, 9,9-difluorononyl, 9,9-difluorodecyl, and 10,10-difluorodecyl.

Specific examples of the alkenyl group having from 2 to 8 carbon atoms and represented by R include vinyl, 1-propenyl, allyl, 1-butenyl, 3-butenyl, isoprenyl, 1-pentenyl, 3-pentenyl, 4-pentenyl, dimethylallyl, 1-hexenyl, 3-hexenyl, 5-hexenyl, 1-heptenyl, 3-heptenyl, 6-heptenyl, and 7-octenyl.

Examples of the linear alkyl group represented by X are those indicated above with respect to R. Examples of the linear alkoxy group having from 1 to 10 carbon atoms represented by X include methoxy, ethoxy, n-propoxy, n-butoxy, n-pentoxy, n-hexyloxy, n-heptyloxy, n-octyloxy, n-nonyloxy and n-decyloxy. Examples of the alkoxyalkyl group having from 2 to 7 carbon atoms represented by X include methoxymethyl, ethoxymethyl, propoxymethyl, butoxymethyl, pentoxymethyl, hexyloxymethyl, methoxyethyl, ethoxyethyl, propoxyethyl, butoxyethyl, pentoxyethyl, methoxypropyl, ethoxypropyl, propoxypropyl, butoxypropyl, methoxybutyl, ethoxybutyl, propoxybutyl, methoxypentyl, ethoxypentyl and methoxyhexyl.

The mono or difluoroalkyl groups having from 1 to 10 carbon atoms and represented by X are those defined with respect to R.

The alkenyl groups having from 2 to 8 carbon atoms and represented by X are those defined with respect to R.

The silacyclohexane compounds of the formulas (I) and (II) essentially have the moiety of the following formula

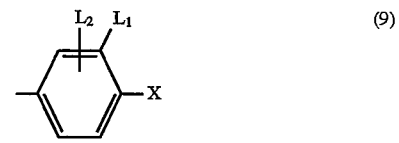

Specific examples of the moiety include residues of the following formulas

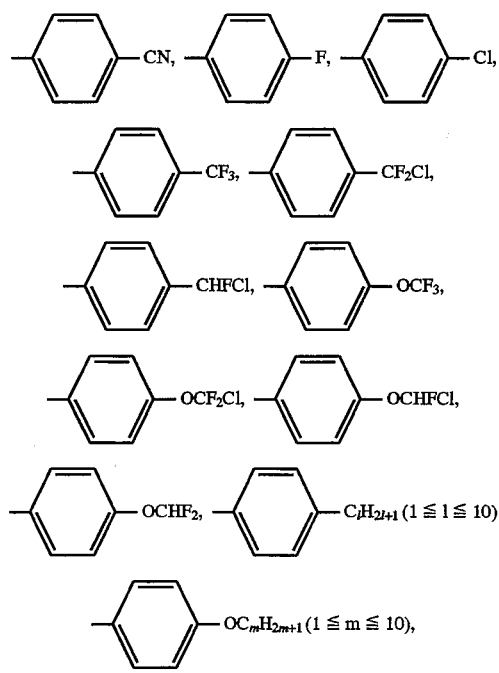

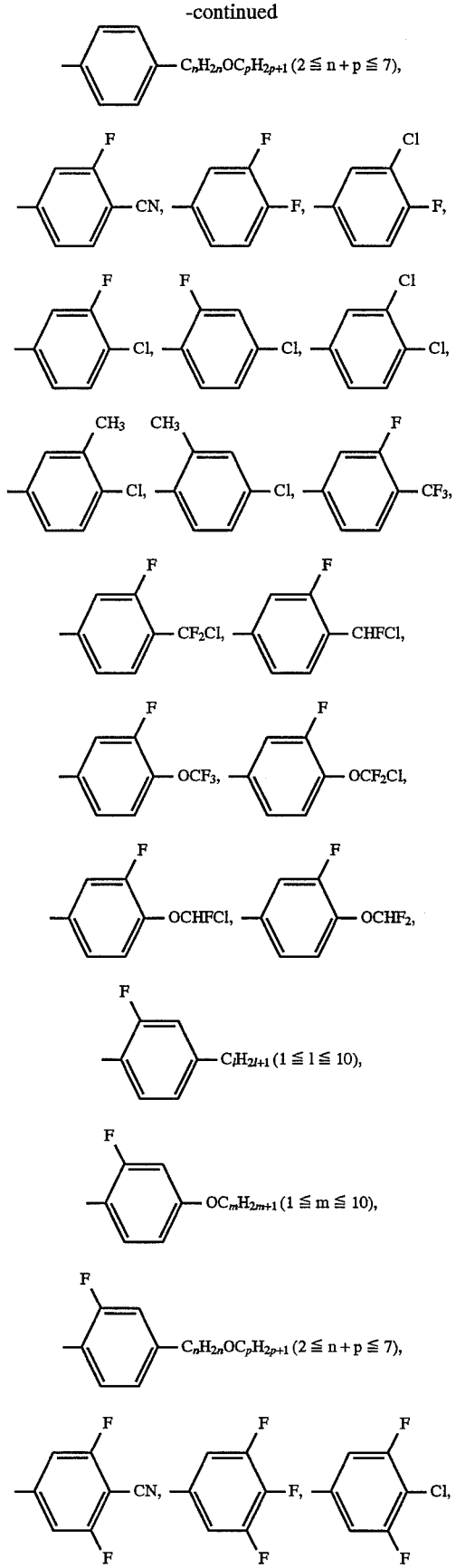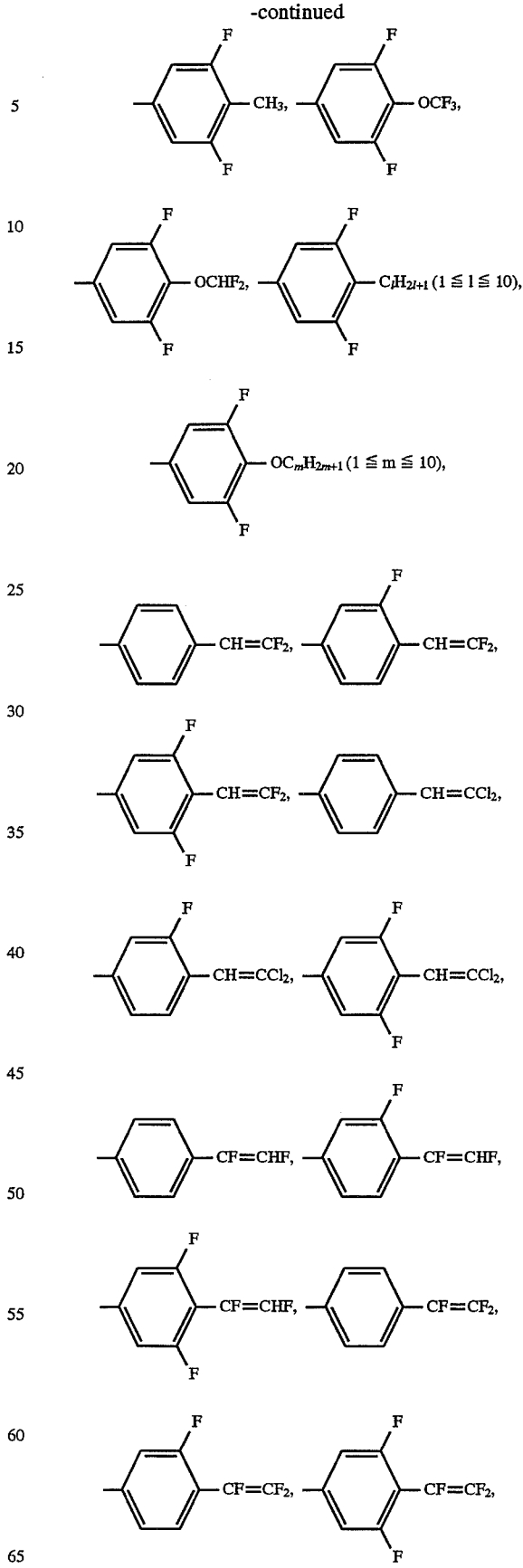

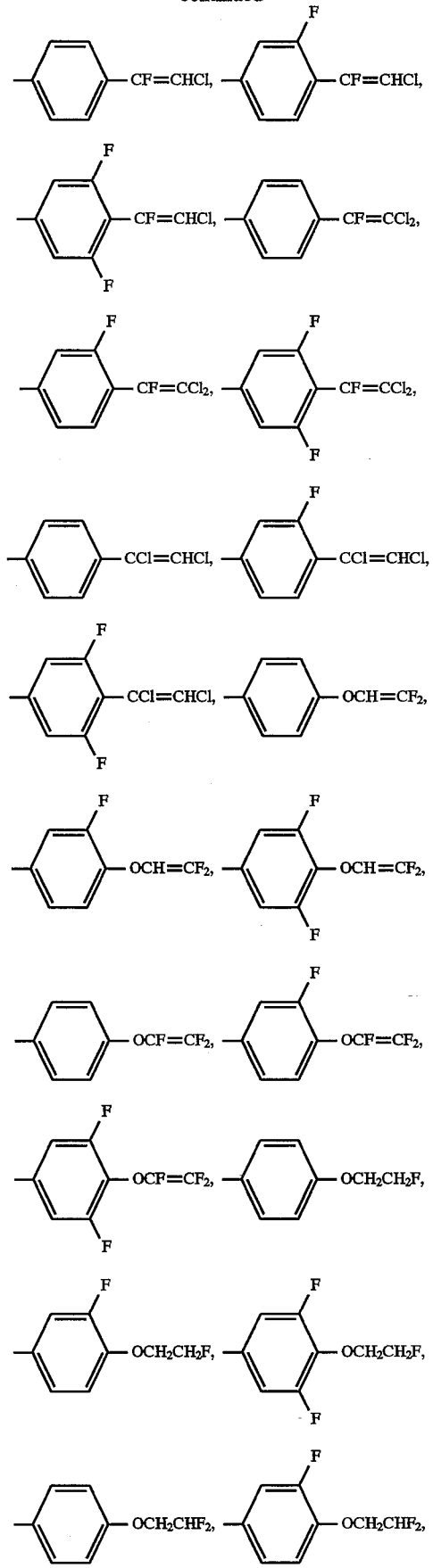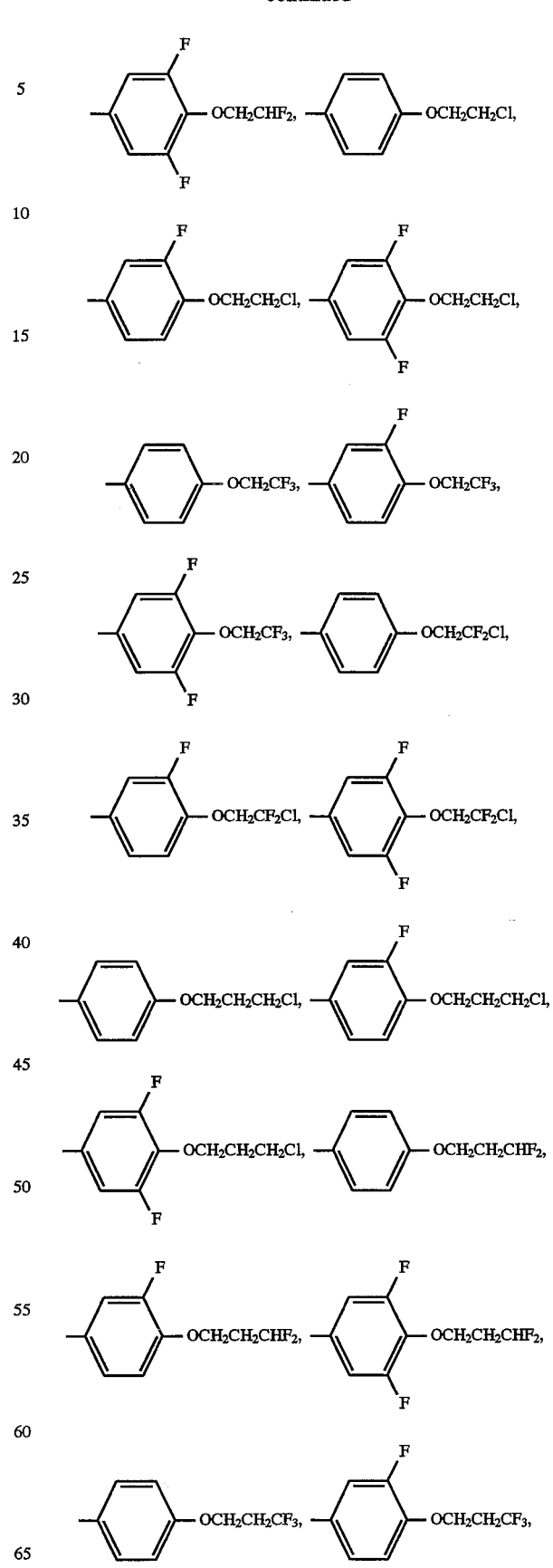

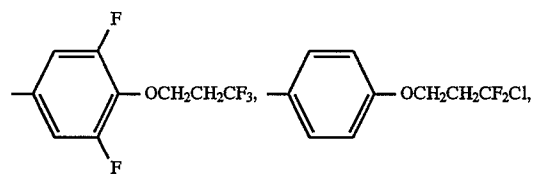
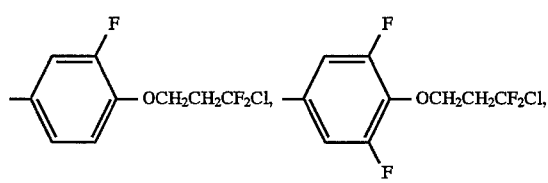
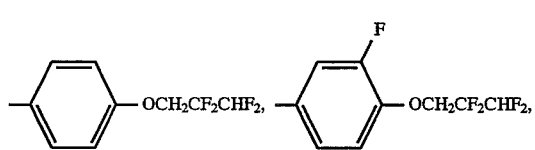
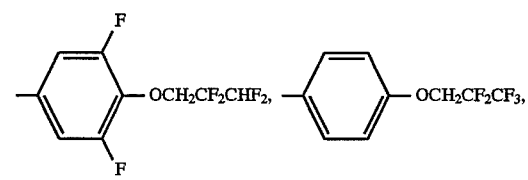
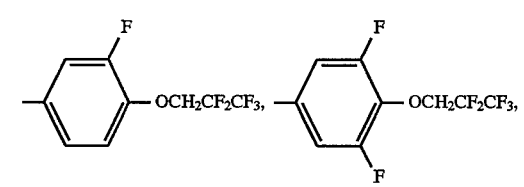
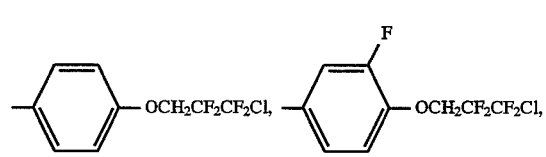
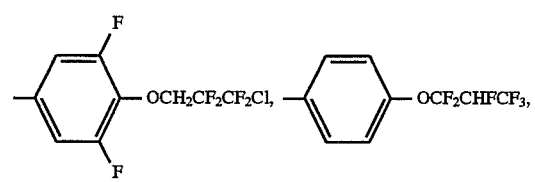
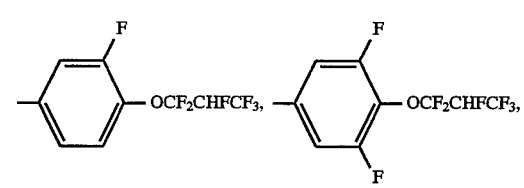
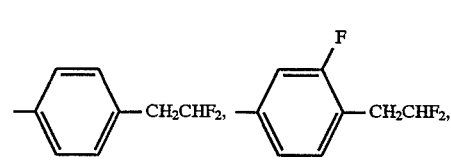
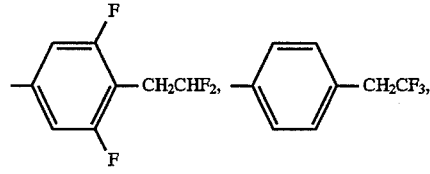
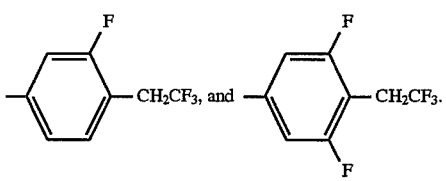

Preferred silacyclohexane compounds include those of the aforeindicated formulas (Ia), (IIa), (IIc) and (IIe) shown below:

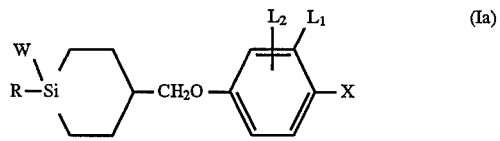

(Ia)

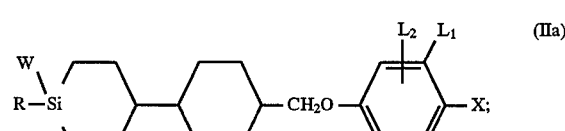

(IIa)

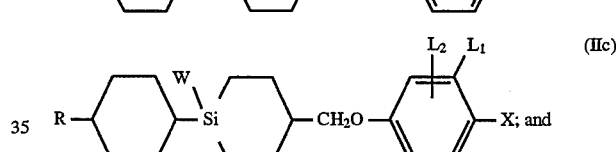

(IIc)

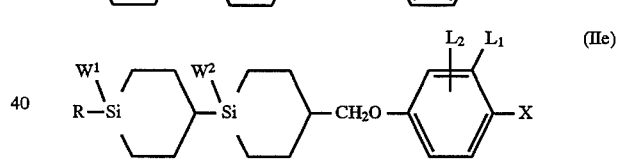

(IIe)

Preferred groups represented by R include: linear alkyl groups having from 2 to 7 carbon atoms, e.g. ethyl, n-propyl, n-butyl, n-pentyl, n-hexyl and n-heptyl; branched alkyl groups having from 3 to 8 carbon atoms, such as isopropyl, 1-methylpropyl, 2-methylpropyl, 1-methylbutyl, 2-methylbutyl, 3-methylbutyl, 1-methylpentyl, 2-methylpentyl and 2-ethylhexyl; alkoxyalkyl groups having from 2 to 6 carbon atoms, such as methoxymethyl, methoxyethyl methoxypropyl, methoxypentyl, ethoxymethyl, ethoxyethyl, propoxymethyl and pentoxymethyl; mono or difluoroalkyl groups having from 2 to 7 carbon atoms, such as 2-fluoroethyl, 2-fluoropropyl, 2-fluorobutyl, 2-fluoropentyl, 2-fluorohexyl, 2-fluoroheptyl, 4-fluorobutyl, 4-fluoropentyl, 4-fluorohexyl, 4-fluoroheptyl, 5-fluoropentyl, 5-fluorohexyl, 5-fluoroheptyl, 6-fluorohexyl, 6-fluoroheptyl, 7-fluoroheptyl, 2,2-difluoroethyl, 2,2-difluoropropyl, 2,2-difluorobutyl, 2,2-difluoropentyl, 2,2-difluorohexyl, 2,2-difluoroheptyl, 4,4-difluorobutyl, 4,4-difluoropentyl, 4,4-difluorohexyl, 4,4-difluoroheptyl, 5,5-difluoropentyl, 5,5-difluorohexyl, 5,5-difluoroheptyl, 6,6-difluorohexyl, 6,6-difluoroheptyl and 7,7-difluoroheptyl; and alkenyl groups having from 2 to 8 carbon atoms, such as vinyl group, 1-propenyl group, 3-butenyl group, 1-pentenyl group, 3-pentenyl group, 4-pentenyl group, 1-hexenyl group, 5-hexenyl group, 6-heptenyl group and 7-octenyl group.

Preferred atoms or groups represented by W, $W_1$ and $W_2$ include H, F or $CH_3$.
Preferred moieties represented by the formula (9)
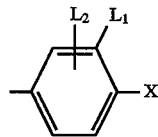
are those indicated below
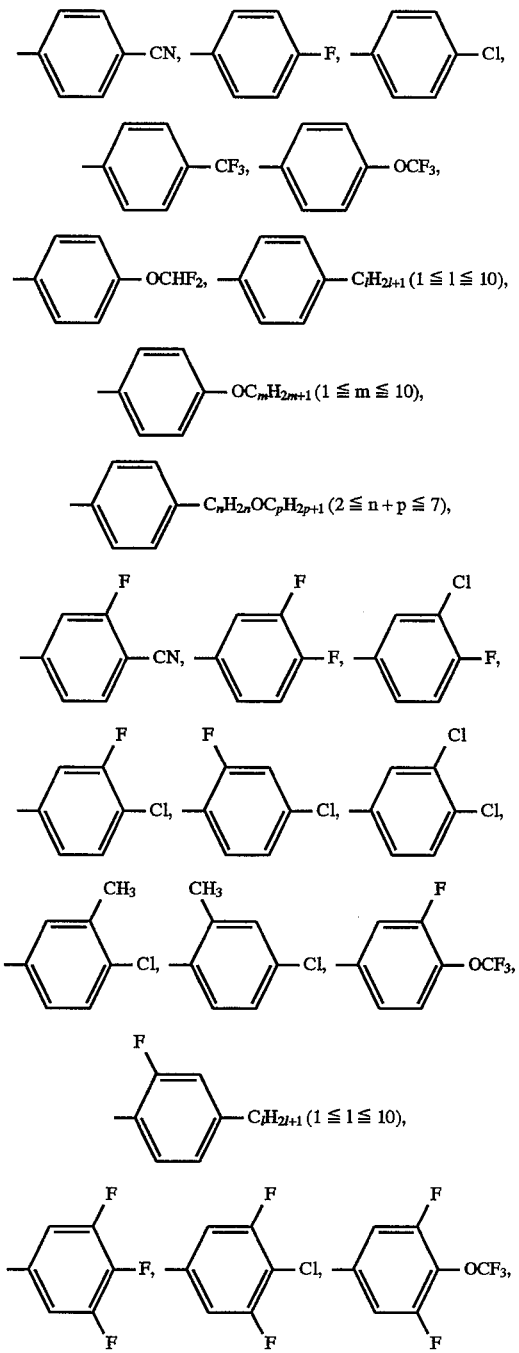
-continued
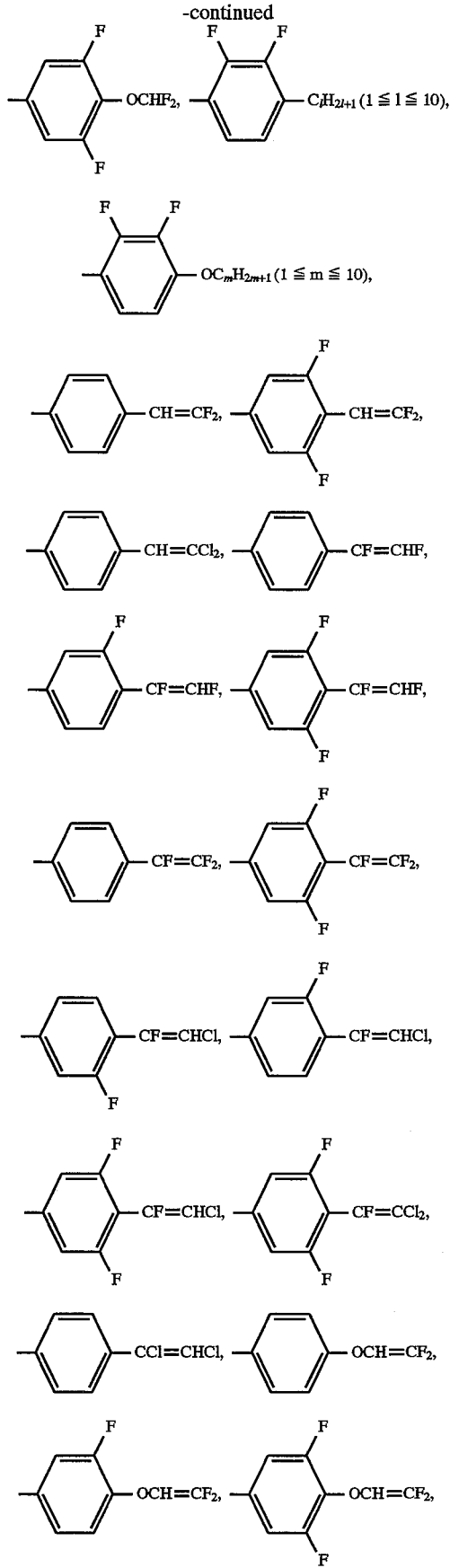

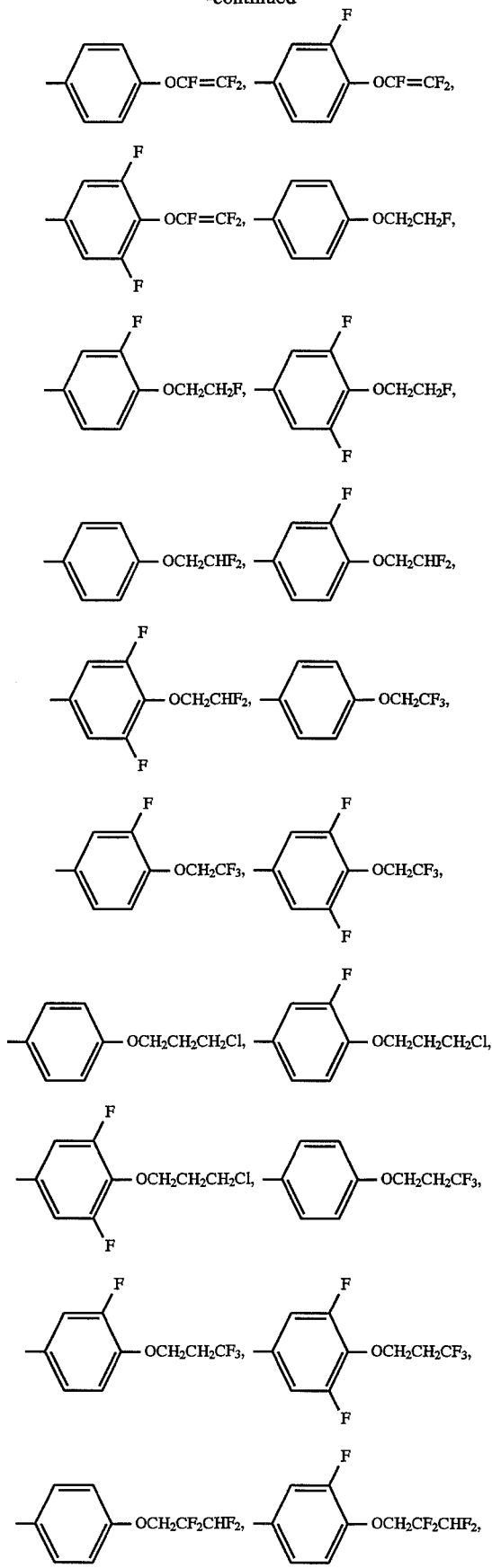
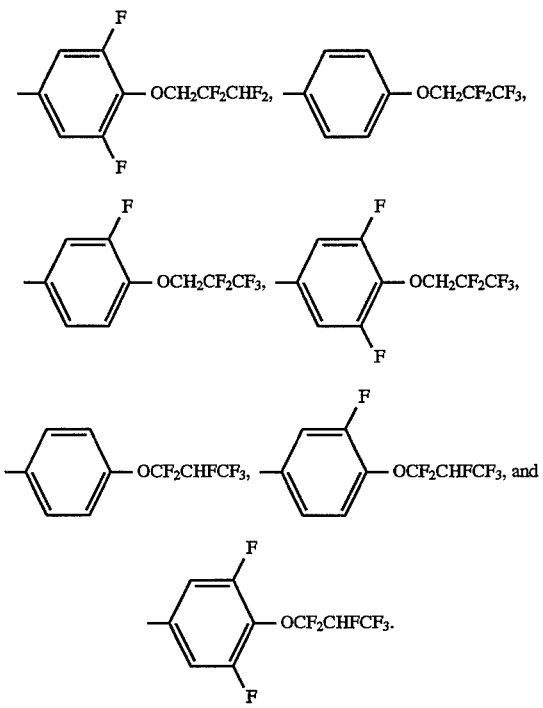
Of these, the compounds having the moieties of the following formulas exhibit a value of Δε close to zero
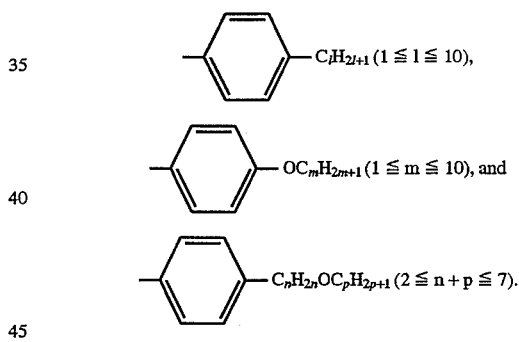
Moreover, the compounds having moieties of the following formulas exhibit a negative value of Δε
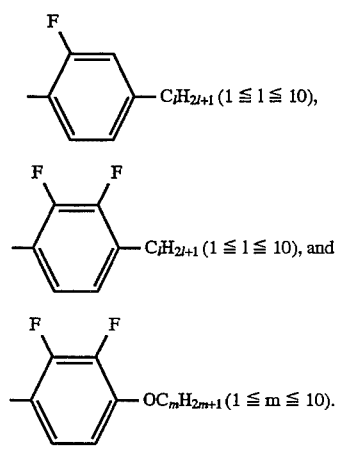

These compounds are suitable for use in DS-type, DAP-type or GH-type display devices.

The preparation of the silacyclohexane compound of the formula (I) according to the invention is now described.

An organometallic reagent or compound of the formula, R-M, wherein M represents Li, MgP or ZnP wherein P is a halogen atom, and R is as defined hereinbefore, is reacted with a compound of the general formula (1)

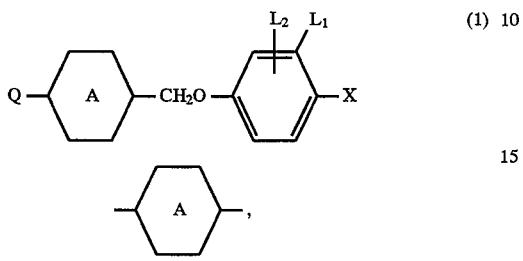

$L_1$, $L_2$ and X are, respectively, as defined in the formula (I), and Q represents a halogen atom, an alkoxy group having from 1 to 4 carbon atoms, a methanesulfonyloxy group, a benzenesulfonyloxy group, a p-toluenesulfonyloxy group or a trifluoromethanesulfonyloxy group. In the reaction, when

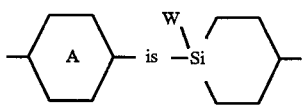

wherein W is H, F, Cl or $CH_3$, Q should preferably be a halogen atom or an alkoxy group. More preferably, Q is Cl, Br, $OCH_3$ or $OCH_2CH_3$ by which the carbon-silicon bonding reaction readily proceeds in high yield. The reaction is conducted under conditions of a temperature preferably ranging from 0° to 150° C. for a time of from 1 to 5 hours.

On the other hand, when

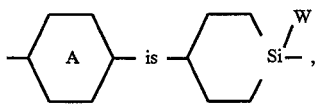

the carbon-carbon bonding reaction is caused to proceed in the presence of a copper salt. Examples of the copper salt include copper (I) salts such as copper (I) chloride, copper (I) bromide, copper (I) iodide, copper (I) cyanide and the like, and copper (II) salts such as copper (II) chloride, copper (II) bromide, copper (II) iodide, copper (II) acetate and the like. Besides, copper complexes such as dilithium tetrachlorocuprate may also be used. In the case, Q in the formula (1) should preferably be a halogen atom or a sulfonyloxy group. More preferably, Q is Br or I. By this, a high yield of an intended product is expected.

The reaction is usually carried out in a solvent such as ethyl ether, tetrahydrofuran, dimethoxyethane, diglyme or the like.

The preparation of the starting compound of the formula (1) is briefly described using reaction sequences (a) and (b) shown below.

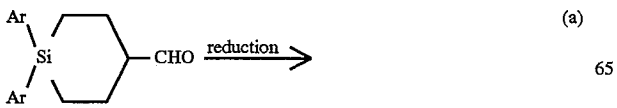

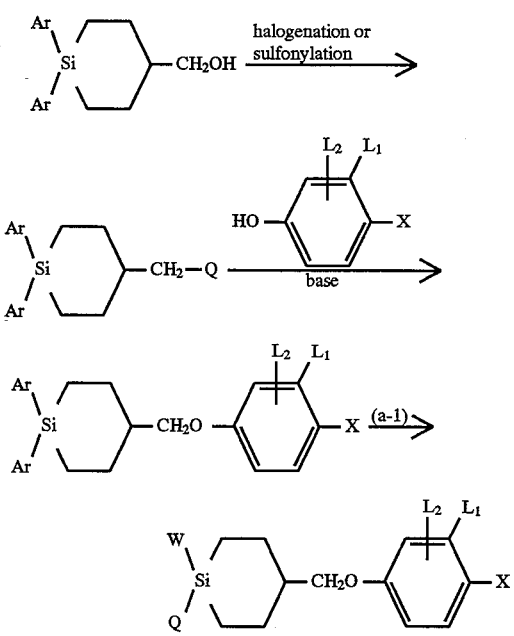

wherein W is as defined before and Q is preferably a halogen such as Br or Cl or an alkoxy group such as methoxy or ethoxy.

The starting aldehyde compound is set out, for example, in Japanese Patent Application No. 6-123208 (corresponding to U.S. patent application Ser. No. 08/434814). The ether bond formation reaction is conducted as set out herein. The product obtained through the final step is a typical compound. This conversion reaction (a-1) is conducted in a manner as set out in Japanese Patent Application No. 6-205931 (corresponding to U.S. patent application Ser. No. 08/511816). The final product may be alkylated or methylated to provide a methyl-substituted compound.

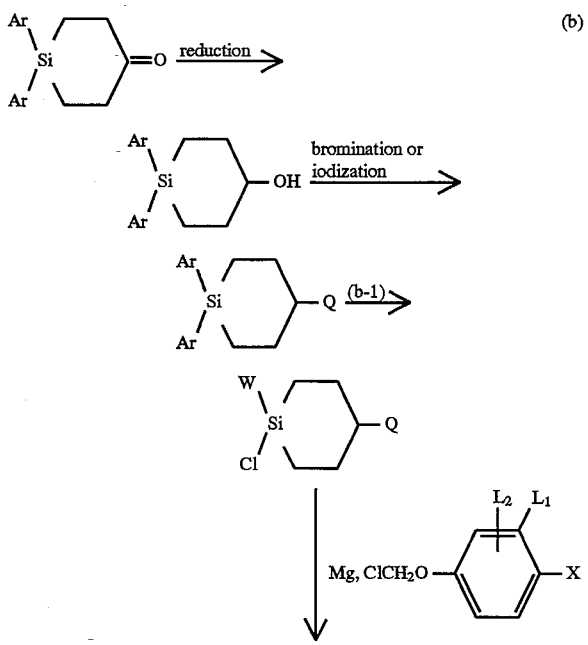

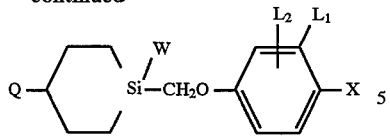

In the above reaction sequence, the starting cyclohexanone compound is prepared for example, by a process set out in U.S. patent application Ser. No. 408961. The conversion reaction (b-1) including halogenation is conducted by a procedure as stated in Japanese Patent Application No. 6-205931. It will be noted that in the above reaction sequence, Ar is phenyl or tolyl, Q is a halogen or a sulfonyloxy group, W is H, F, Cl or methyl, and X, $L_1$ and $L_2$ are, respectively, as defined hereinbefore. Typical of the final product in the above sequence is a compound of the following formula

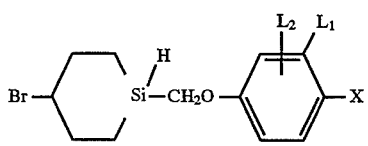

Likewise, if alkylated, a methyl-substituted compound can be obtained.

Alternatively, the compound of the formula (I) may be prepared from a phenolic compound of the following general formula (2)

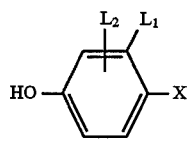  (2)

wherein $L_1$, $L_2$ and X are, respectively, as defined hereinbefore, with a compound of the following general formula (3) in the presence of a base

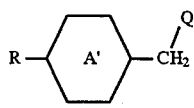  (3)

wherein R is as defined hereinbefore, Q is preferably a halogen atom or a sulfonyloxy group as set out hereinbefore, more preferably Br, I, benzenesulfonyloxy, p-toluenesulfonyloxy or the like, and

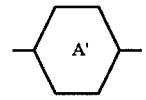

is a trans-1-sila-1,4-cyclohexylene group or trans-4-sila-1,4-cyclohexylene group or trans-4-sila-1,4-cyclohexylene group having methyl or Ar wherein Ar is phenyl or tolyl at the 1 or 4 position, thereby obtaining a compound of the general formula (I).

The bases used in the above reaction include 1) metal hydrides such as sodium hydride, potassium hydride, calcium hydride and the like, 2) alkoxides such as sodium methoxide, sodium ethoxide, potassium t-butoxide and the like, 3) alkyl lithium compounds such as n-butyl lithium, sec-butyl lithium and the like, 4) inorganic bases such as potassium carbonate, sodium carbonate, sodium hydroxide, potassium hydroxide and the like, and 5) organic bases such as triethylamine, pyridine, 4-dimethylaminopyridine and the like.

Chlorosilacylohexanes, fluorosilacyclohexanes and hydrosilacyclohexanes are, respectively, readily derived from corresponding arylsilacyclohexane compounds obtained from the above reaction according to the following reaction sequence (10) wherein only the moiety taking part in the conversion reaction is shown

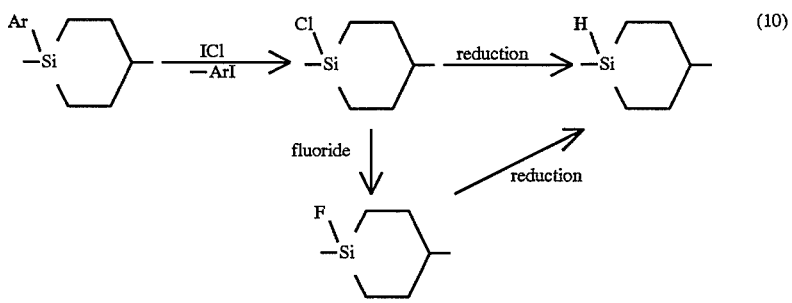  (10)

wherein Ar represents a phenyl or tolyl group.

As will be apparent from the above reaction sequence, when iodine monochloride is reacted with the arylsilacyclohexane compound, a chlorosilacyclohexane compound of the formula (Ia) or (Ib) wherein W is Cl is obtained through the halo de-silylation reaction. The de-silylation reaction may be caused in a wide range of temperatures. Preferably, the temperature used is in the range of from 0° to 80° C., more preferably from 10 to 40° C. The reaction is usually conducted in a halogenated hydrocarbon solvent such as chloroform, carbon tetrachloride, methylene chloride or the like.

When the resultant chlorosilacyclohexane compound is reacted with fluorides such as cesium fluoride, copper (I) fluoride, antimony fluoride, zinc fluoride, calcium fluoride, tetra-n-butylammonium fluoride and the like, a fluorosilacyclohexane compound of the formulas (Ia) to (Ib) wherein W is fluorine is obtained. This reaction is carried out preferably at a temperature of from 0° C. to a refluxing temperature of a solvent used. Examples of the solvent include hydrocarbons such as heptane, hexane benzene, toluene and the like.

When the chlorosilacyclohexane or fluorosilacyclohexane compound is reacted with a reducing agent under mild conditions, a hydrosilacyclohexane compound of the formula (Ia) or (Ib) wherein W is hydrogen is obtained. Examples of the reducing agent include metal hydrides such as sodium hydride, calcium hydride, trialkylsilanes, boranes, dialkyl aluminium compounds and the like, and complex hydrides such as lithium aluminium hydride, sodium borohydride, lithium borohydride, potassium borohydride, tributylammonium borohydride and the like. Although not limitative, the reduction of the halosilacyclohexane is carried out preferably at a temperature of from −50° to 100° C., more preferably from −20° to 70° C. The reaction is usually carried out in a solvent such as ethers diethyl ether, tetrahydrofuran and the like, and aromatic hydrocarbons such as benzene, toluene and the like.

If the thus obtained product is in the form of steric isomers, a trans isomer can be isolated and purified through known purification procedures such as recrystallization, chromatography and the like.

The compound of the above formula (3) can be prepared, for example, according to the following reaction sequences (c) and (d) wherein Ar may be replaced by methyl.

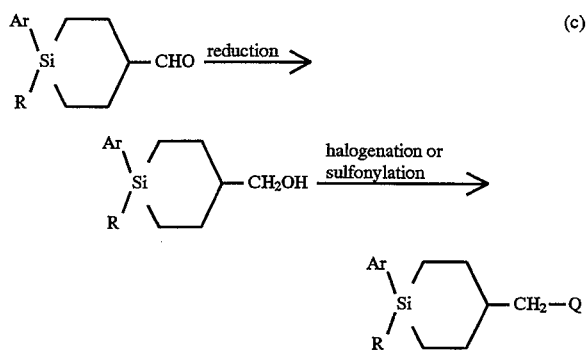

The starting compound of the above sequence (c) is prepared in the same manner as in sequence (a) according to a procedure as set out in Japanese Patent Application No.6-123208. The compound of the formula (3) is subjected to the ether bonding reaction with the compound of the formula (2), followed by conversion to a chlorosilacyclohexane, fluorosilacyclohexane or hydrosilacyclohexane through reaction as shown in the formula (10). This conversion reaction may be conducted in a manner as set out, for example, in Japanese Patent Application No. 6-163065 (corresponding to U.S. patent application Ser. No. 08/491141).

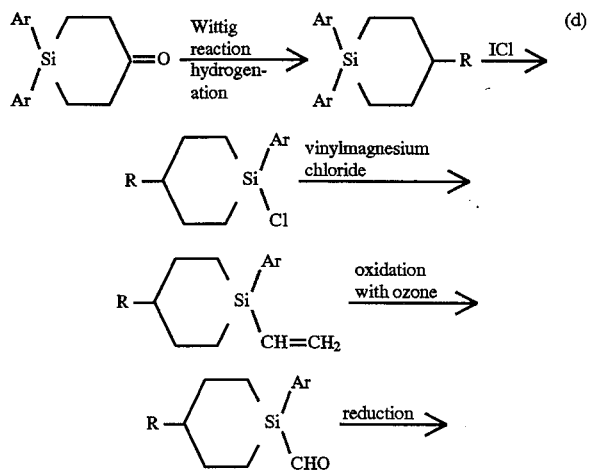

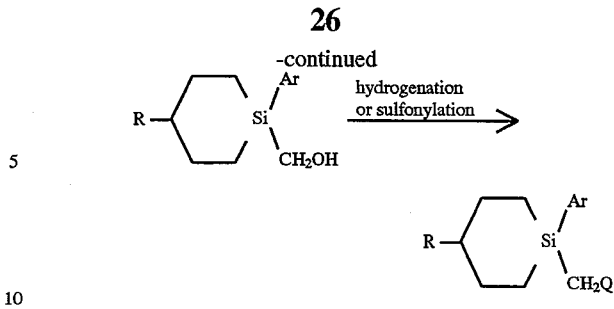

Next, the preparation of the silacyclohexane compound of the general formula (II) is described.

Like the preparation of the compound (I), an organometallic reagent of the formula, R-M, wherein M represents Li, MgP or ZnP wherein P is a halogen atom, and R is as defined hereinbefore, is reacted with a compound of the general formula (4)

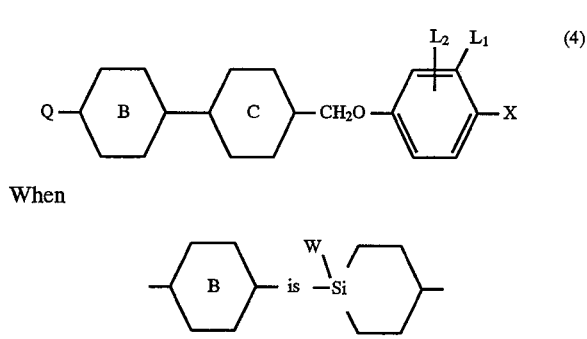

When

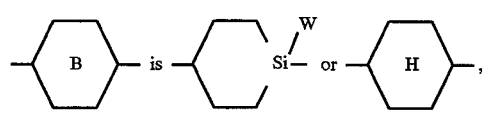

wherein W is H, F, Cl or CH$_3$, Q should preferably be a halogen atom or an alkoxy group. More preferably, Q is Cl, Br, OCH$_3$ or OCH$_2$CH$_3$, by which the carbon-silicon bonding reaction with R-M readily proceeds in high yield. The reaction favorably proceeds under conditions of a temperature preferably ranging from 0° to 150° C. for a time of from 1 to 5 hours. On the other hand, when

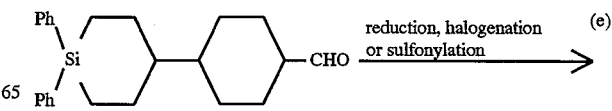

the carbon-carbon bonding reaction is caused to proceed in the presence of a copper salt as defined with respect to the compounds of the formula (I). Q in the formula (4) should preferably be a halogen atom or a sulfonyloxy group. More preferably, Q is Br or I. By this, a high yield of sa intended product is expected.

The reaction is usually carried out in a halogenated hydrocarbon solvent such as chloroform, carbon tetrachloride, methylene chloride or the like.

The starting compound of the formula (4) is prepared in the same manner as in (a) set out hereinbefore. This is schematically shown, for example, in the following reaction sequence (e) wherein Ph is phenyl.

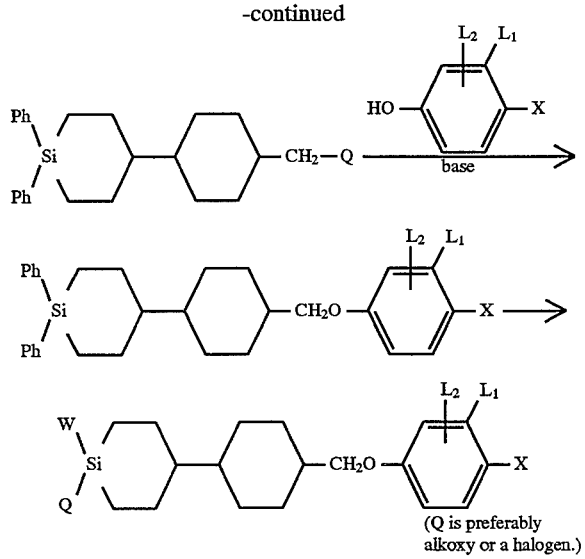

The starting compound of the sequence (e) is prepared according to the process set out in Japanese Patent Application No. 6-182904 (corresponding to U.S. patent application Ser. No. 08/501524). The respective steps proceed substantially in the same manner as in the sequence (a).

Alternatively, the compound (II) may be prepared by a process which comprises subjecting the carbon-carbon bonding reaction or carbon-silicon bonding reaction between an organometallic reagent of the following general formula (5)

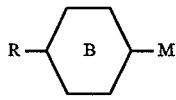

(5)

wherein R and M are, respectively, as defined above, and a compound of the following general formula (6)

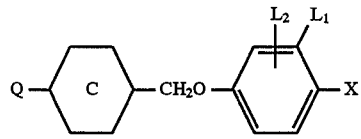

(6)

thereby obtaining a silacyclohexane compound of the general formula (II). In the above reaction, if

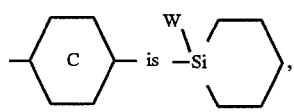

Q should preferably be a halogen atom or an alkoxy group. More preferably, Q is Cl, Br, OCH$_3$ or OCH$_2$CH$_3$, by which the carbon-silicon bonding reaction proceeds readily to obtain an intended product in high yield. On the other hand, when

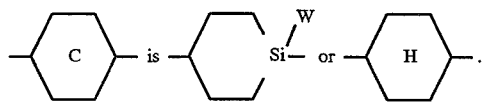

the carbon-carbon bonding reaction is caused to proceed in the presence of a copper salt as defined hereinbefore. In this case, Q in the formula (6) should preferably be a halogen atom or a sulfonyloxy group. More preferably, Q is Br or I. By this, a high yield of an intended product is achieved.

The reaction is caused to proceed under conditions of a temperature of from 0° to 150° C. in a solvent such as ethyl ether, tetrahydrofuran, dimethoxyethane, diglyme or the like.

The preparation of the compound of the formula (5) which is free of any silicon atom in the structure thereof is known in the art and is not described herein. The compound of the formula (5) which contains a silicon atom therein is prepared, for example, according to the following reaction sequence (f).

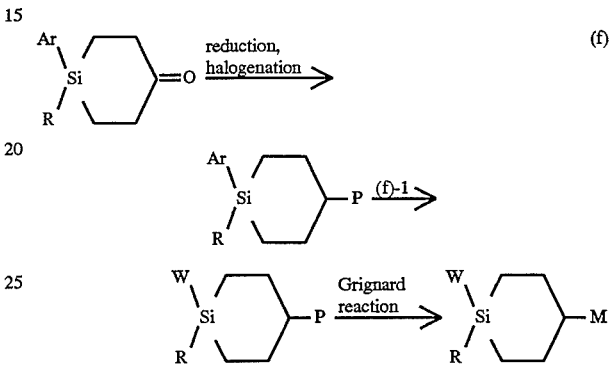

(f)

wherein Ar, R, P, W and M are, respectively, as defined hereinbefore. The substitution of Ar with W in (f)-1 has been described hereinbefore. This process proceeds in a manner as set out in Japanese Patent Application No. 6-163065.

The compounds of the formula (6) which have a trans-1-sila-1,4-cyclohexylene ring or a trans-4-sila-1,4-cyclohexylene ring can be prepared according to the processes shown in (a) and (b) illustrated hereinbefore. A compound of the following formula having no silicon atom in the structure therein can be prepared, for example, according to the reaction sequence (g).

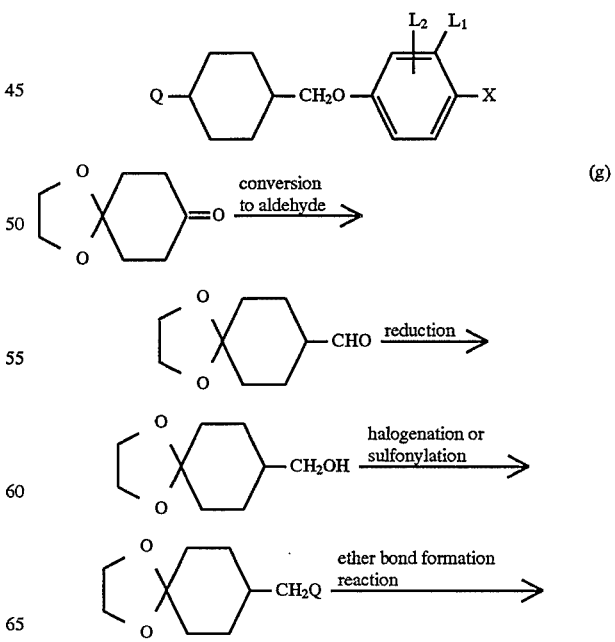

(g)

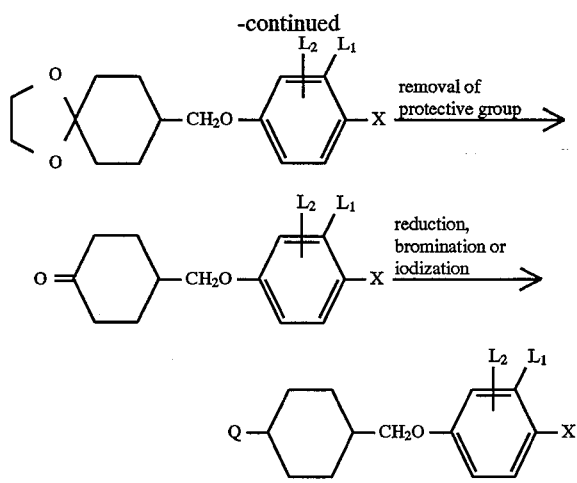

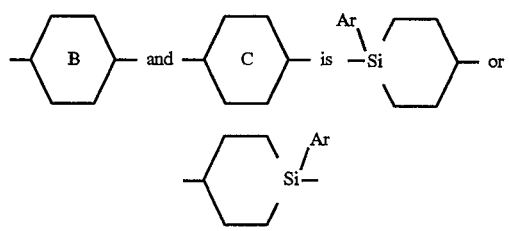

The coupling reaction between the compounds of the formulas (5) and (6) enables one to prepare the silacyclohexane compounds of the afore-indicated formulas (IIa), (IIc), (IId), (IIe) and (IIg). Still alternatively, the compound of the formula (II) may he prepared from a phenolic compound of the following general formula (7)

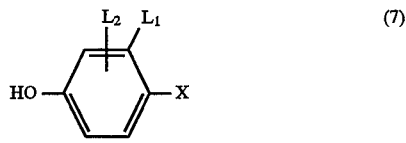

wherein $L_1$, $L_2$ and X are, respectively, as defined hereinbefore, with a compound of the following general formula (8)

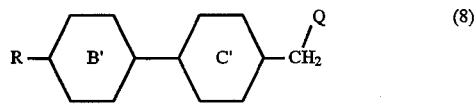

wherein R and Q are, respectively, as defined hereinabove, and one of

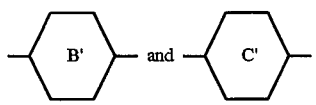

is a trans-1-sila-1,4-cyclohexylene group or trans-4-sila-1,4-cyclohexylene group wherein Si at the 1 or 4 position is substituted with a methyl group or Ar wherein Ar is phenyl or tolyl, and the other is a trans-1-sila-1,4-cyclohexylene group or trans-4-sila-1,4-cyclohexylene group substituted as defined above, or a trans-1,4-cyclohexylene group, in the presence of a base to obtain a compound of the general formula (II).

The bases used in the above reaction are those set out with respect to the preparation of the compound (I).

Chlorosilacylohexanes, fluorosilacyclohexanes and hydrosilacyclohexanes of the general formula (II) can be readily obtained from those compounds of the formula (II) wherein at least one of in the same manner as in the preparation of the compound (I). More particularly, the chlorosilacydohexane compounds of the formulas (IIa) to (IIg) wherein W is chlorine can be obtained through halo-desilylation reaction of a corresponding phenyl or tolyl-substituted silacyclohexane compound. Likewise, fluorosilacyclohexane and hydrosilacyclohexane compounds may be prepared as with the compound (I).

The starting compounds of the formula (8) are prepared according to the following procedures (h) to (n).

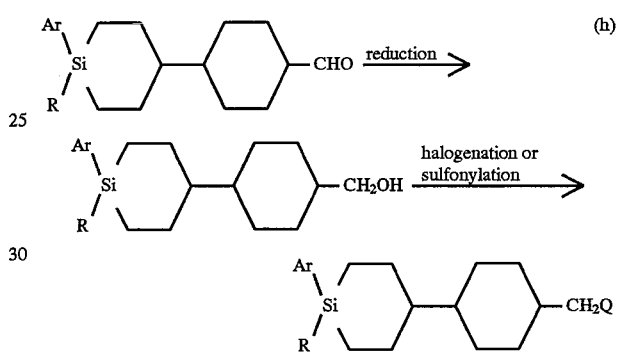

The starting aldehyde is set out in Japanese patent application No. 6-182904, from which the final compound of the formula (8) can be readily obtained as shown above.

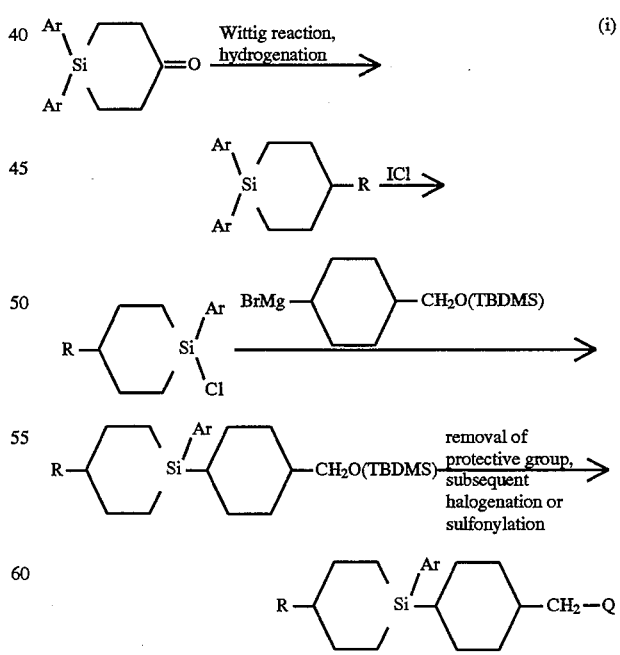

In the above sequence, TBDMS is a t-butyldimethylsilyl protective group, and Ar may be replaced by methyl in (i) and also in subsequent (j) to (n).

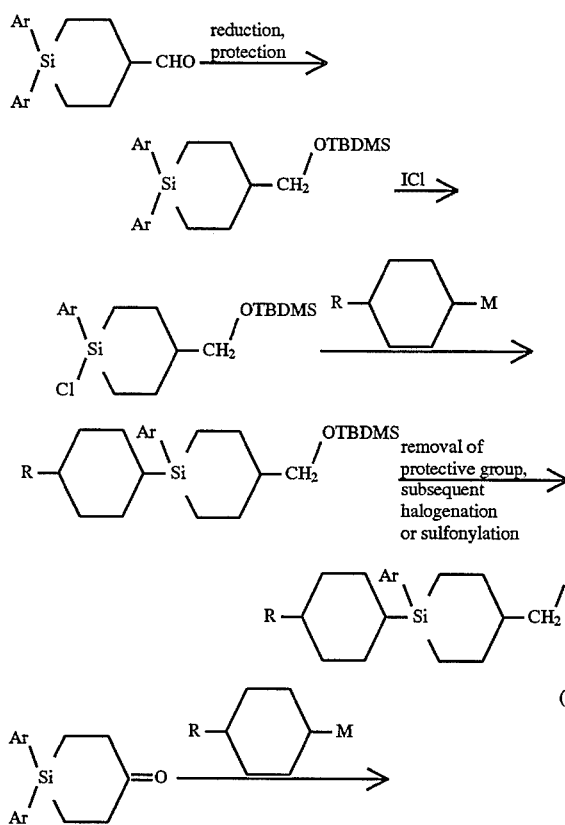
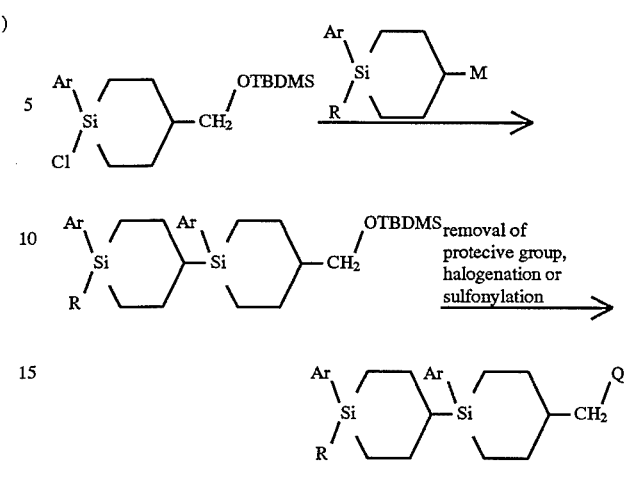
It will be noted that the compound of the following formula
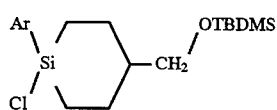
used as one of the reactants in the above sequence can be prepared in the following manner.
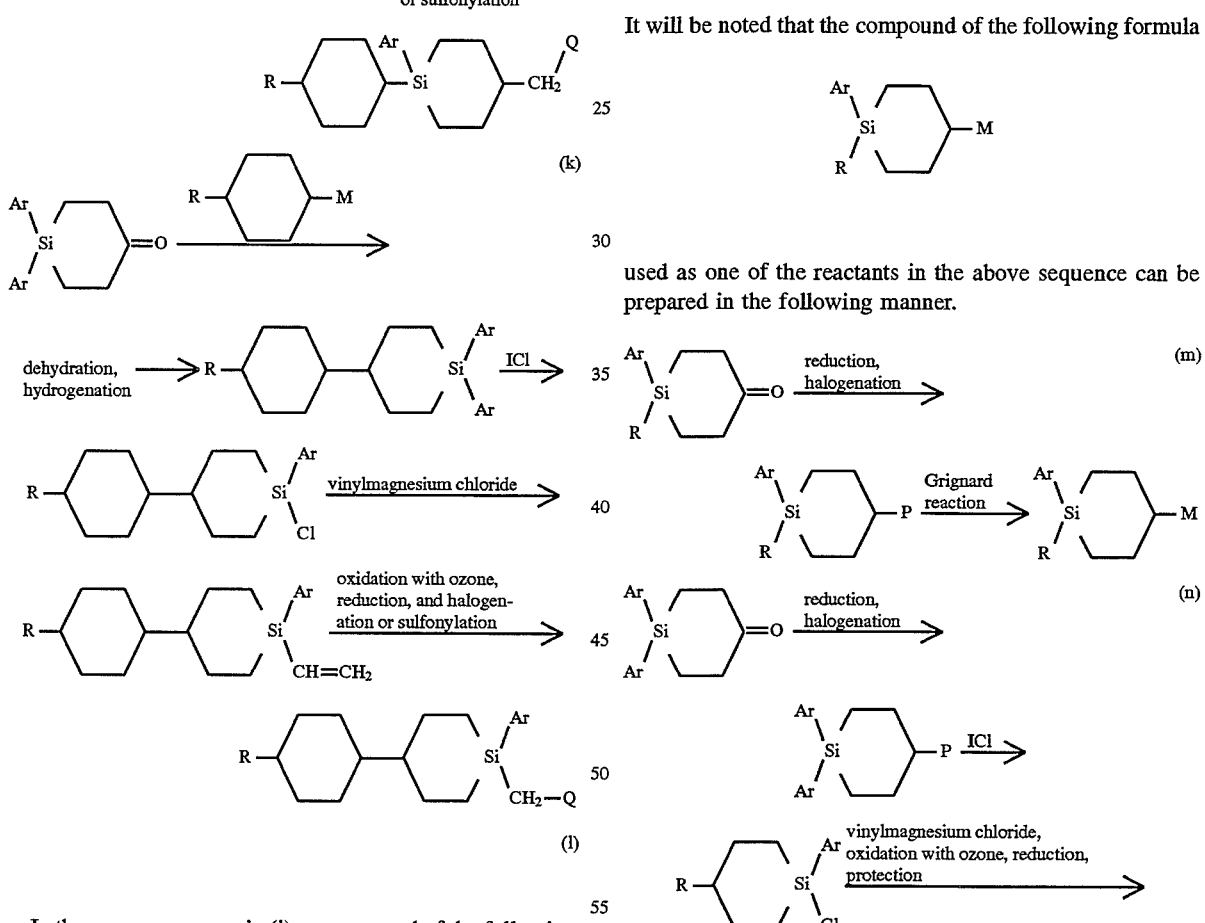
In the same manner as in (j), a compound of the following formula is obtained
Then, this compound is reacted according to the following reaction sequence.

-continued

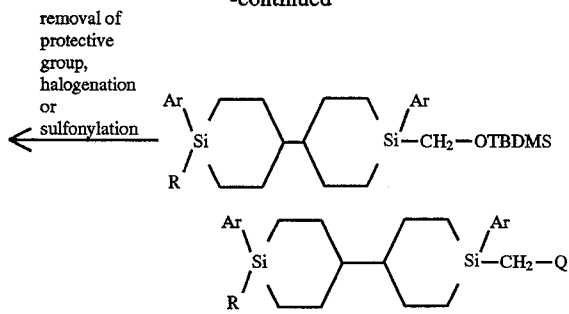

In the same manner as in (m) just above,

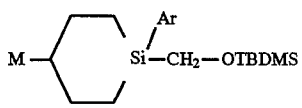

is obtained. This compound is reacted in the same manner as in (i), followed by further reactions according to the following reaction sequence.

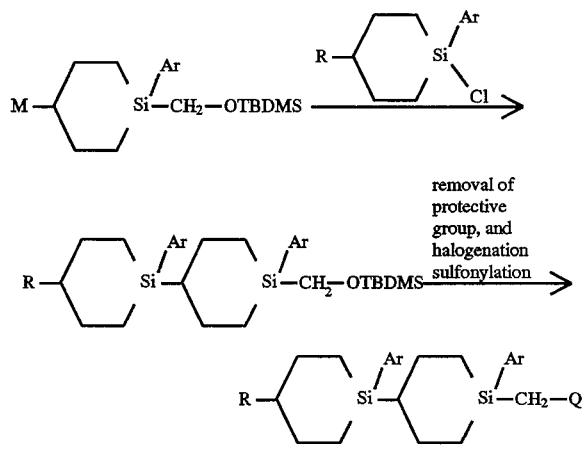

As will be apparent from (h) to (n), all the types of silacyclohexane compounds of the formula (8) wherein the silicon atom or atoms are positioned at the 1 and/or 4 positions can be prepared. These compounds are subjected to ether bond formation reaction with the compound of the formula (7), followed by halo-desilylation and reduction to obtain hydrosilacyclohexane compounds.

If the thus obtained products are in the form of steric isomers, a trans-trans isomer can be isolated and purified through known purification procedures such as recrystallization, chromatography and the like.

The silacyclohexane compounds of the formulas (I) and (II) of the invention are conveniently used in combination with known liquid crystal compounds to provide liquid crystal compositions. Such known liquid crystal compounds suitable for this purpose include those compounds of the general formulas (11) and (12)

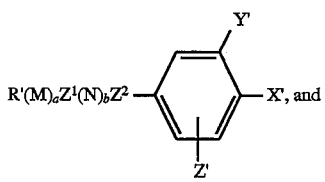

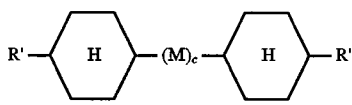

In the above formula (11) and (12), each R' represents a linear alkyl group having from 1 to 10 carbon atoms, a branched alkyl group having from 3 to 8 carbon atoms, an alkoxyalkyl group having from 2 to 7 carbon atoms or an alkenyl group having from 2 to 8 carbon atoms as defined in the afore-indicated formula (I) or (II); X' represents a linear alkyl group having from 1 to 10 carbon atoms, a linear alkoxy group having from 1 to 10 carbon atoms, an alkoxyalkyl group having from 2 to 7 carbon atoms, CN, F, Cl, $CF_3$, $CF_2Cl$, $CHFCl$, $OCF_3$, $OCF_2Cl$, $OCHFCl$, $OCHF_2$; Y' and Z' independently represent H, F, Cl or $CH_3$; M and N independently represent (1) an unsubstituted or substituted trans-1,4-cyclohexylene group which has, if substituted, one or more substituents such as F, Cl, Br, CN and an alkyl group having from 1 to 3 carbon atoms, (2) a trans-1,4-cyclohexylene group wherein one $CH_2$ unit or two $CH_2$ units, not adjacent each other, of the cyclohexane ring are replaced by O or S, (3) a 1,4-cyclohexenylene group, (4) an unsubstituted or substituted 1,4-phenylene group having, if substituted, one or two F, Cl, $CH_3$ and/or CN groups and (5) a 1,4-phenylene group in which one or two CH units of the phenylene group are replaced by nitrogen atom, a and h are, respectively, 0, 1 or 2 provided that a +b=1, 2 or 3, and c is 0, 1 or 2; and $Z^1$ and $Z^2$ are, respectively, —$CH_2CH_2$—, —CH=CH—, —C≡C—, —$CO_2$—, —OCO—, —$CH_2O$—, —$OCH_2$—or single bond.

In the above formulas (11) and (12), if a, b and/or c is 2, M's and/or N's may be the same or different and are independently selected from the groups (1) to (5) set forth above.

The silacyclohexane compounds which may be used singly or in combination should preferably be present in a liquid crystal phase or composition in an amount of from 1 to 50 mole %, preferably from 5 to 30 mole %. As a matter of course, the liquid crystal composition may further comprise polychromatic dyes capable of forming colored guest-host systems, and additives capable of imparting dielectric anisotropy, viscosity modifiers, additives for changing the direction of alignment of a nematic phase.

In practice, the liquid crystal phase or composition comprising at least one compound of the invention is used as a liquid crystal display device wherein the composition is hermetically sealed between transparent substrates each having an electrode of a desired shape. If necessary, the device may have various types of undercoatings, overcoatings for controlling the alignment, a polarizer, a filter and a reflective layer as is known in the art. Alternatively, a multi-layer cell may be used to incorporate the compounds of the invention. The liquid crystal display device may be used in combination with other types of display devices, semiconductor substrates, and light sources.

With the compounds of the invention whose value of Δε is positive or is close to zero, the liquid crystal display device is driven according to a twisted nematic (TN) system, a super twisted nematic (STN) system or a guest-host (GH)

system. In the case of the compounds whose value of Δε is negative, a dynamics scattering mode (DSM) system, an electrically controlled birefringence (ECB) system, a guest-host (GH) system and the like known in the art may be adopted.

The invention is more particularly described by way of examples.

EXAMPLE 1

Preparation of trans-4-(3,4-difluorophenyloxymethyl)-1-n-pentyl-1-silacyclohexane 3.0 g (20 mmols) of n-pentyl bromide was dropped in a mixture of 0.5 g of magnesium (21 mmols) and 50 ml of tetrahydrofuran (hereinafter referred to simply as THF) to obtain a Grignard reagent. Subsequently, the solution was dropped in 50 ml of a THF solution of 5.5 g (20 mmols) of 4-(3,4-difluorophenyloxymethyl)-1-chloro-1-silacyclohexane to obtain a crude product. This product was found to be a mixture of trans and cis isomers with respect to the silacyclohexane ring. The product was after-treated by a usual manner and isolated through column chromatography to obtain 5.6 g (yield: 89%) of the intended trans isomer product. The results of measurement of a phase transition temperature and the IR analysis are shown below.

$T_{CI}$ (crystal-isotropic phase transition temperature)=−9.1° C.

IR (liquid film) $v_{max}$: 2918, 2854, 2100, 1516, 1468, 1213, 1205, 1161, 978, 891, 831 $cm^{-1}$

EXAMPLE 2

Preparation of trans-4-(3,4,5-trifluorophenyloxymethyl)-1-n-heptyl-1-silacyclohexane The general procedure of Example 1 was repeated using n-heptyl bromide and 4-(3,4,5-trifluorophenyloxymethyl)-1-chloro-1-silacyclohexane, thereby obtaining the intended product.

EXAMPLE 3

Preparation of trans-4-(4-chloro-3-fluorophenyloxymethyl)-1-n-heptyl-1-silacyclohexane The general procedure of Example 1 was repeated using n-heptyl bromide and 4-(4-chloro-3-fluorophenyloxymethyl)-1-chloro-1-silacyclohexane, thereby obtaining the intended product.

EXAMPLE 4

Preparation of trans-4-(4-chlorophenyloxymethyl)-1-n-pentyl-1-silacyclohexane

The general procedure of Example 1 was repeated using 4-(4-chlorophenyloxymethyl)-1-chloro-1-silacyclohexane, thereby obtaining the intended product. The results of measurement of a phase transition temperature and IR analysis are shown below.

$T_{CI}$ (crystal phase-isotropic phase transition temperature): 19.5° C.

IR (liquid film) $v_{max}$: 2918, 2854, 2100, 1493, 1466, 1246, 970, 889, 822 $cm^{-1}$

EXAMPLE 5

Preparation of trans-4-(4-cyanophenyloxymethyl)-1-fluoro-l-n-pentyl-1-silacyclohexane The general procedure of Example 1 was repeated using 4-(4-cyanophenyloxymethyl)-1-chloro-1-fluoro-1-silacyclohexane, thereby obtaining the intended product.

EXAMPLE 6

Preparation of trans-4-(4-fluorophenyloxymethyl)-1-n-pentyl-1-silacyclohexane

The general procedure of Example 1 was repeated using 4-(4-fluorophenyloxymethyl)-1-chloro-1-silacyclohexane, thereby obtaining the intended product. The results of measurement of phase transition temperatures and IR analysis are shown below.

$T_{CI}$ (crystal phase-isotropic phase transition temperature) =19.4° C. $T_{NI}$ (nematic phase-isotropic phase transition temperature)=−43.1° C.

IR (liquid film) $v_{max}$: 2918, 2854, 2100, 1506, 1468, 1250, 1219, 970, 889, 825 $cm^{-1}$

EXAMPLE 7

Preparation of trans-4-(4-methoxyphenyloxymethyl)-1-methyl-1-n-heptyl-1-silacyclohexane The general procedure of Example 1 was repeated using n-heptyl bromide and 4-(4-methoxyphenyloxymethyl)-1-chloro-1-methyl-1-silacyclohexane, thereby obtaining the intended product.

EXAMPLE 8

Preparation of trans-4-(4-chloro-3,5-difluorophenyloxymethyl)-1-(3-methylbutyl)-1-silacyclohexane The general procedure of Example 1 was repeated using 3-methylbutyl bromide and 4-(4-chloro-3,5-difluorophenyloxymethyl)-1-chloro-1-silacyclohexane, thereby obtaining the intended product.

EXAMPLE 9

Preparation of trans-4-(4-trifluoromethoxyphenyloxymethyl)-1-n-pentyl-1-silacyclohexane 8.3 g (60 mmols) of potassium carbonate was added to a mixture of 6.8 g (20 mmols) of 4-bromomethyl-1-n-pentyl-1-phenyl-1-silacyclohexane, 3.6 g (20 mmols) of 4-trifluoromethoxyphenol and 50 ml of dimethylformamide (DMF), followed by heating under flux for 10 hours. The reaction mixture was after-treated by a usual manner and purified through chromatography to obtain 6.4 g (yield: 73%) of 4-(4-trifluoromethoxyphenyloxymethyl)-1-n-pentyl-1-phenyl-1-silacyclohexane. The results of IR and NMR analyses are shown below.

IR (liquid film) $v_{max}$: 2918, 2856, 1506, 1468, 1267, 1246, 1200, 1165, 968, 827 $cm^{-1}$ $^1$H-NMR (CDCl$_3$) δ:0.6–2.3 (20H, m), 3.6–3.8 (2H, dd), 6.7–7.0 (2H, m), 7.0–7.2 (2H, m), 7.3–7.6 (5H, m) ppm 2.5 ml of a carbon tetrachloride solution of 1.0 mol of iodine monochloride was added to a mixture of 0.87 g (2.0 mmols) of the thus obtained product and 15 ml of carbon tetrachloride, followed by agitation for 1 hour. The reaction mixture was concentrated under reduced pressure to obtain 0.76 g (yield: 96%) of 4-(4-trifluoromethoxyphenyloxymethyl)-1-chloro-1-n-pentyl-1-silacyclohexane. The results of gas chromatographymass spectroscopy are shown below. GC-MS (M/2)$^+$: 394, 323, 287, 205, 147, 119

0.39 g (1.0 mmol) of the product was added to a mixture of 100 mg of lithium aluminium hydride and 20 ml of THF, followed by agitation at −20° C. for 15 minutes. The reaction mixture was poured into dilute hydrochloric acid and after-treated by a usual manner. The resultant crude product consisted of a mixture of trans and cis isomers with respect to the silacyclohexane ring. Hence, the product was purified through chromatography to obtain 0.20 g (yield: 55%) of the intended trans isomer. The results of measurement of a phase transition temperature and IR analysis are shown below.

$T_{CI}$ (crystal phase-isotropic phase transition temperature) =15.3° C.

IR (liquid film) $v_{max}$: 2918, 2854, 2100, 1508, 1468, 1246, 1200, 1163, 891, 829 cm$^{-1}$

EXAMPLE 10

Preparation of trans-4-(4-trifluoromethoxy-phenyloxymethyl)-1-n-heptyl-1-silacyclohexane The general procedure of Example 9 was repeated using 4-bromomethyl-1-n-heptyl-1-phenyl-1-silacyclohexane, thereby obtaining the intended compound.

EXAMPLE 11

Preparation of trans-4-(3,4-difluorophenyloxymethyl-1-n-heptyl-1-silacyclohexane The general procedure of Example 9 was repeated using 3,4-difluorophenol and 4-bromomethyl-1-n-heptyl-1-phenyl-1-silacyclohexane, thereby obtaining the intended compound.

EXAMPLE 12

Preparation of trans-4-(3-fluoro-4-trifluoro-methoxyphenyloxymethyl)-1-n-heptyl-1-silacyclohexane The general procedure of Example 9 was repeated using 3-fluoro-4-trifluoromethoxyphenol and 4-bromomethyl-1-n-heptyl-1-phenyl-1-silacyclohexane, thereby obtaining the intended compound.

EXAMPLE 13

Preparation of trans-4-(3,5-difluoro-4-difluorormethoxyphenyloxymethyl)-1-n-heptyl-1-silacyclohexane The general procedure of Example 9 was repeated using 3,5-difluoro-4-difluoromethoxyphenol and 4-bromomethyl-1-n-heptyl-1-phenyl-1-silacyclohexane, thereby obtaining the intended compound.

EXAMPLE 14

Preparation of trans-4-(4-n-propylphenyloxymethyl)-1-n-pentyl-1-silacyclohexane

The general procedure of Example 9 was repeated using 4-n-propyphenol, thereby obtaining the intended compound.

EXAMPLE 15

Preparation of trans-4-(2,3-difluoro-4-ethoxy-phenyloxymethyl)-1-n-heptyl-1-silacyclohexane The general procedure of Example 9 was repeated using 2,3-difluoro-4-ethoxyphenol and 4-bromomethyl-1-n-heptyl-1-phenyl-1-silacyclohexane, thereby obtaining the intended compound.

EXAMPLE 16

Preparation of trans-4-(2,3-difluoro-4-ethoxy-phenyloxymethyl)-1-n-pentyl-1-silacyclohexane The general procedure of Example 9 was repeated using 2,3-difluoro-4-ethoxyphenol, thereby obtaining the intended compound. The results of measurement of a phase transition temperature and IR analysis are shown below.

$T_{CI}$ (crystal phase-isotropic phase transition temperature) =17.4° C.

IR (liquid film) $v_{max}$: 2918, 2854, 2100, 1508, 1468, 1273, 1068, 985, 891, 833 cm$^{-1}$

EXAMPLE 17

Preparation of trans-4-(4-trifluoromethylphenyloxymethyl)-1-(5-methoxypentyl)-4-silacyclohexane The general procedure of Example 9 was repeated using 4-trifluoromethylphenol and 4-bromomethyl-1-(5-methoxypentyl)-4-phenyl-4-silacyclohexane, thereby obtaining the intended compound.

EXAMPLE 18

Preparation of trans-4-(4-ethoxyphenyloxymethyl)-1-(4-pentenyl)-4-silacyclohexane The general procedure of Example 9 was repeated using 4-ethoxyphenol and 4-bromomethyl$_1$-(4-pentenyl)-4-phenyl-4-silacyclohexane, thereby obtaining the intended compound.

EXAMPLE 19

Preparation of trans-4-(4-difluoromethoxyphenyloxmethyl)-1-n-heptyl-4-silacyclohexane The general procedure of Example 9 was repeated using 4-difluoromethoxyphenol and 4-bromomethyl-1-n-heptyl-4-phenyl-4-silacyclohexane, thereby obtaining the intended compound.

EXAMPLE 20

Preparation of trans-4-(4-cyano-3-fluorophenyloxymethyl)-1-n-pentyl-1-silacyclohexane The general procedure of Example 9 was repeated using 4-cyano-3-fluorophenol, thereby obtaining the intended compound.

EXAMPLE 21

Preparation of trans-4-(2,3-difluoro-4-n-propylphenyloxymethyl)-1-n-pentyl-1-silacyclohexane The general procedure of Example 9 was repeated using 2,3-difluoro-4-n-propylphenol, thereby obtaining the intended compound.

EXAMPLE 22

Preparation of trans-4-(4-chloro-2-fluorophenyloxymethyl)-1-n-heptyl-1-silacyclohexane The general procedure of Example 9 was repeated using 4-chloro-2-fluorophenol and 4-bromomethyl-1-n-heptyl-1-phenyl-1-silacyclohexane, thereby obtaining the intended compound.

EXAMPLE 23

Preparation of trans-4-(4-chloro-3-methylphenyloxymethyl)-1-n-heptyl-1-silacyclohexane The general procedure of Example 9 was repeated using 4-chloro-3-methylphenol and 4-bromomethyl-1-n-heptyl-1-phenyl-1-silacyclohexane, thereby obtaining the intended compound.

EXAMPLE 24

Preparation of trans-4-(3,4-difluorophenyloxymethyl)-1-(4-fluorobutyl)-1-silacyclohexane The general procedure of Example 9 was repeated using 3,4-difluorophenol and 4-bromomethyl-1-(4-fluorobutyl)-1-phenyl-1-silacyclohexane, thereby obtaining the intended compound.

EXAMPLE 25

Preparation of trans-4-(3,4,5-trifluorophenyloxymethyl)-1-(4-fluoropentyl)-1-silacyclohexane The general procedure of Example 9 was repeated using 3,4,5-trifluorophenol and 4-bromomethyl-1-(4-fluoropentyl)-1-phenyl-1-silacyclohexane, thereby obtaining the intended compound.

EXAMPLE 26

Preparation of trans-4-(3,5-difluoro-4-(2,2-difluoroethoxy)phenyloxymethyl)-1-n-pentyl-1-silacyclohexane The general procedure of Example 9 was repeated using 3,5-difluoro-4-(2,2-difluoroethoxy)phenol thereby obtaining the intended compound.

EXAMPLE 27

Preparation of trans-4-(3-fluoro-4-(2,2,3,3,3-pentafluoropropoxy)phenyloxymethyl)-1-n-heptyl-1-silacyclohexane The general procedure of Example 9 was repeated using 3-fluoro-4-(2,2,3,3,3-pentafluoropropoxyphenol) and 4-bromomethyl-1-n-heptyl-1-phenyl-1-silacyclohexane, thereby obtaining the intended compound.

EXAMPLE 28

Preparation of trans-4-(3-fluoro-4-(2,2,2-trifluoroethoxy)phenyloxymethyl)-1-n-heptyl-1-silacyclohexane The general procedure of Example 9 was repeated using 3-fluoro-4-(2,2,2-trifluoroethoxy)phenol and 4-bromomethyl-1-n-heptyl-1-phenyl-1-silacyclohexane, thereby obtaining the intended compound.

EXAMPLE 29

Preparation of trans-4-(3,5-difluoro-4-(2,2,3,3-tetrafluoropropoxy)phenyloxymethyl)-1-n-pentyl-1-silacyclohexane The general procedure of Example 9 was repeated using 3,5-difluoro-4-(2,2,3,3-tetrafluoropropoxy)phenol, thereby obtaining the intended compound.

EXAMPLE 30

A liquid crystal mixture A was prepared by mixing 40% by mole of 4-(4-(trans-4-ethylcyclohexyl)-trans-4-cyclohexyl)-1,2-difluorobenzene, 35% by mole of 4-(4-(trans-4-n-propylcyclohexyl)-trans-4-cyclohexyl)-1,2-difluorobenzene, and 25% by mole of 4-(4-(trans-4-(trans-4-n-pentylcyclohexyl)-trans-4-cyclohexyl)-1,2-difluorobenzene. The mixture had the following properties.

$T_{CN}$ (crystal phase-nematic phase transition temperature): 7° C.

$T_{NI}$ (nematic phase-isotropic phase transition temperature): 106° C.

Threshold voltage; 2.50 V

Viscosity (20° C.): 26 cps.

A mixture consisting of 85% by mole of the mixture A and 15% by mole of trans -4-(4-fluorophenyloxymethyl)-1-n-pentyl-1-silacyclohexane had the following properties.

$T_{CN}$ (crystal phase-nematic phase transition temperature): 2° C.

$T_{NI}$ (nematic phase-isotropic phase transition temperature): 84° C.

Threshold voltage: 2.35 V

Viscosity (20° C.): 22.0 cps.

As will be apparent from the above examples, the compounds of the formula (I) of present invention contribute to the reduction of viscosity and the lowering of melting point of the mixed liquid crystal composition.

EXAMPLE 31

Preparation of trans-4-(trans-4-(3,4-difluorophenyloxymethyl)cyclohexyl)-1-n-propyl-1-silacyclohexane 2.5 g (20 mmols) of n-propyl bromide was dropped in a mixture of 0.5 g of magnesium (21 mmols) and 50 ml of THF to obtain a Grignard reagent. Subsequently, the solution was dropped in 50 ml of a THF solution of 7.2 g (20 mmols) of 4-(trans-4-(3,4-difluorophenyloxymethyl)cyclohexyl)-1-chloro-1-silacyclohexane to obtain a crude product. This product was found to be a mixture of trans and cis isomers with respect to the silacyclohexane ring. The product was after-treated by a usual manner and isolated through column chromatography to obtain 6.7 g (yield: 91%) of the intended trans-trans isomer product. The results of measurement of phase transition temperatures and the IR analysis are shown below.

$T_{CN}$ (crystal phase-nematic phase transition temperature) =35° C.

$T_{NI}$ (nematic phase-isotropic phase transition temperature)=65° C.

IR (liquid film) $v_{max}$: 2922, 2854, 2098, 1605, 1516. 1161, 989, 887, 843 cm$^{-1}$

EXAMPLE 32

Preparation of trans-4-(trans-4-(3,4,5-trifluorophenyloxymethyl)cyclohexyl)-1-n-propyl-1-silacyclohexane The general procedure of Example 30 was repeated using 4-(trans-4-(3,4,5-trifluorophenyloxymethyl)cyclohexyl)-1-chloro-1-silacyclohexane, thereby obtaining the intended compound.

EXAMPLE 33

Preparation of trans-4-(trans-4-(4-chloro-3-fluorophenyloxymethyl)cyclohexyl)-1-n-propyl-1-silacyclohexane The general procedure of Example 30 was repeated using 4-(trans-4-(4-chloro-3-fluorophenyloxymethyl)cyclohexyl)-1-chloro-1-silacyclohexane, thereby obtaining the intended compound.

EXAMPLE 34

Preparation of trans-4-(trans-4-(4-chlorophenyloxymethyl)cyclohexyl)-1-n-pentyl-1-silacyclohexane The general procedure of Example 30 was repeated using n-pentyl bromide and 4-(trans-4-(4-chlorophenyloxymethyl)cyclohexyl)-1-chloro-1-silacyclohexane, thereby obtaining the intended compound.

EXAMPLE 35

Preparation of trans-4-(trans-4-(4-cyanophenyloxymethyl) cyclohexyl )-1-fluoro-1-n-pentyl-1-silacyclohexane The general procedure of Example 30 was repeated using n-pentyl bromide and 4-(trans-4-(4-cyanophenyloxymethyl) cyclohexyl)-1-fluoro-1-chloro-1-silacyclohexane, thereby obtaining the intended compound.

EXAMPLE 36

Preparation of trans-4-(trans-4-(4-fluorophenyloxymethyl)-1-silacyclohexyl)-1-n-propylcyclohexane 4.1 g (20 mmols) of 4-n-propylcyclohexyl bromide was dropped in a mixture of 0.5 g of magnesium (21 mmols) and 50 ml of THF to obtain a Grignard reagent. Subsequently, the solution was dropped in 50 ml of a THF solution of 5.2 g (20 mmols) of 4-(4-fluorophenyloxymethyl)-1-chloro-1-silacyclohexane to obtain a crude product. This product was found to be a mixture of trans and cis isomers with respect to the silacyclohexane ring and the cyclohexane ring. The product was after-treated by a usual manner and isolated through column chromatography to obtain 6.1 g (yield: 87%) of the intended trans-trans isomer product.

EXAMPLE 37

Preparation of trans-4-(trans-4-(4-methoxyphenyloxymethyl)-1-methyl-1-silacyclohexyl)-1-n-propylcyclohexane The general procedure of Example 36 was repeated using 4-(4-methoxyphenyloxymethyl)-1-methyl-1-chloro-1-silacyclohexane, thereby obtaining the intended product.

EXAMPLE 38

Preparation of trans-4-(trans-4-(4-chloro-3,5-difluorophenyloxymethyl)-1-silacyclohexyl)-1-(3-methylbutyl)cyclohexane The general procedure of Example 36 was repeated using 4-(3-methylbutyl)cyclohexyl bromide and 4-(4-chloro-3,5-difluorophenyloxyrnethyl)-1-chloro-1-silacyclohexane, thereby obtaining the intended product.

EXAMPLE 39

Preparation of trans-4-(trans-4-(4-trifluoromethoxyphenyloxymethyl)cyclohexyl)-1-n-propyl-1-silacyclohexane 8.3 g (60 mmols) of potassium carbonate was added to a mixture of 7.9 g (20 mmols) of 4-(trans-4-bromomethylcyclohexyl)-1-phenyl-1-n-propyl-1-silacyclohexane, 3.6 g (20 mmols) of 4-trifluoromethoxyphenol and 50 ml of dimethylformamide, followed by heating under reflux for 10 hours. The reaction mixture was after-treated by a usual manner and purified through chromatography to obtain 7.0 g (yield: 71%) of 4-(trans-4-(4-trifluoromethoxyphenyloxymethyl) cyclohexyl)-1-phenyl-1-n-propyl-1-silacyclohexane. The results of IR and NMR analyses are shown below.

IR (liquid film) $v_{max}$: 2922, 2858, 1596, 1506, 1246, 1223, 1200, 1163, 985, 840 cm$^{-1}$ $^1$H-NMR (CDCl$_3$) δ: 0.6–2.0 (26H, m), 3.6–3.9 (2H, dd), 6.7–6.9 (2H, m), 7.0–7.2 (2H, m), 7.3–7.6 (5H, m) ppm 2.5 ml of a carbon tetrachloride solution of 1.0 mol of iodine monochloride was added to a mixture of 1.00 g (2.0 mmols) of the thus obtained product and 15 ml of carbon tetrachloride at room temperature and agitated for 1 hour.

The reaction mixture was concentrated under reduced pressure to obtain 860 mg (yield: 96%) of trans-4-(trans-4-(4-trifluoromethoxyphenyloxymethyl)cyclohexyl)-1-chloro-1-n-propyl-1-silacyclohexane. The results of GC-MS are shown below. GC-MS (m/z)$^+$: 488, 270, 242, 178, 119

450 mg (1.0 mmol) of the product was added to a mixture of 100 mg of lithium aluminium hydride and 20 ml of THF, followed by agitation at −20° C. for 15 minutes. The reaction mixture was poured into dilute hydrochloric acid and after-treated by a usual manner. The resultant crude product consisted of trans and cis isomers with respect to the silacyclohexane ring. These isomers were separated through chromatography to obtain 250 mg (yield: 60%) of a trans-trans isomer product. The results of measurement of phase transition temperatures and IR analysis are shown below.

$T_{CN}$ (crystal phase-nematic phase transition temperature)= 28° C.

$T_{CS}$ (crystal phase-smectic phase transition temperature) =5° C.

$T_{NI}$ (nematic phase-isotropic phase transition temperature)=94° C.

IR (liquid film) $v_{max}$: 2922, 2854, 2100, 1612, 1506, 1244, 1200, 1165, 989, 887, 840 cm$^{-1}$

EXAMPLE 40

Preparation of trans-4-(trans-4-(4-trifluoromethoxyphenyloxymethyl)cyclohexyl)-1-n-pentyl-1-silacyclohexane The general procedure of Example 39 was repeated using 4-(trans-4-bromomethylcyclohexyl)-1-phenyl-1-n-pentyl-1-silacyclohexane, thereby obtaining the intended product. The results of measurement of phase transition temperatures and IR analysis are shown below.

$T_{CN}$ (crystal phase-nematic phase transition temperature) =45° C.

$T_{NI}$ (nematic phase-isotropic phase transition temperature)=90° C.

IR (liquid film) $v_{max}$: 2920, 2852, 2100, 1612, 1508, 1244, 1200, 1165, 989, 887, 833 cm$^{-1}$

EXAMPLE 41

Preparation of trans-4-(trans-4-(3,4-difluorophenyloxymethyl)cyclohexyl)-1-n-pentyl-1-silacyclohexane The general procedure of Example 39 was repeated using 3,4-difluorophenol and 4-(trans-4-bromomethylcyclohexyl)-1-phenyl-1-n-pentyl-1-silacyclohexane, thereby obtaining the intended product. The results of measurement of phase transition temperatures and IR analysis are shown below.

$T_{CN}$ (crystal phase-nematic phase transition temperature) =28° C.

$T_{NI}$ (nematic phase-isotropic phase transition temperature)=68° C.

IR (liquid film) $v_{max}$: 2920, 2852, 2100, 1605, 1516, 1161, 991, 887, 831 cm$^{-1}$

EXAMPLE 42

Preparation of trans-4-(trans-4-(3-fluoro-4-trifluoromethoxyphenyloxymethyl)cyclohexyl)-1-n-propyl-1-silacyclohexane The general procedure of Example 39 was repeated using 3-fluoro-4-trifluoromethoxyphenol, thereby obtaining the intended product.

EXAMPLE 43

Preparation of trans-4-(trans-4-(3,5-difluoro-4-difluoromethoxyphenyloxymethyl)cyclohexyl)-1-n-propyl-1-silacyclohexane The general procedure of Example 39 was repeated using 3,5-difluoro-4-difluoromethoxyphenol, thereby obtaining the intended product.

EXAMPLE 44

Preparation of trans-4-(trans-4-n-propylphenyloxymethyl)cyclohexyl)-1-n-pentyl-1-silacyclohexane The general procedure of Example 39 was repeated using 4-n-propylphenol and 4-(trans-4-bromomethylcyclohexyl)-1-phenyl-1-n-pentyl-1-silacyclohexane, thereby obtaining the intended product.

EXAMPLE 45

Preparation of trans-4-(trans-4-(2,3-difluoro-4-ethoxyphenyloxymethyl)cyclohexyl)-1-n-propyl-1-silacyclohexane The general procedure of Example 39 was repeated using 2,3-difluoro-4-ethoxyphenol, thereby obtaining the intended product. The results of measurement of phase transition temperatures and IR analysis are shown below.

$T_{CN}$ (crystal phase-nematic phase transition temperature) =50° C.

$T_{NI}$ (nematic phase-isotropic phase transition temperature)=119° C.

IR (KBr, disc) $v_{max}$: 2927, 2852, 2085, 1506, 1468, 1273, 1068, 972, 889, 843 cm$^{-1}$

EXAMPLE 46

Preparation of trans-4-(trans-4-(2,3-difluoro-4-ethoxyphenyloxymethyl)cyclohexyl)-1-n-pentyl-1-silacyclohexane The general procedure of Example 39 was repeated using 2,3-difluoro-4-ethoxyphenol and 4-(trans-4-bromomethylcyclohexyl)-1-phenyl-1-n-pentyl-1-silacyclohexane, thereby obtaining the intended product. The results of measurement of phase transition temperatures and IR analysis are shown below.

$T_{CN}$ (crystal phase-nematic phase transition temperature) =50° C.

$T_{NI}$ (nematic phase-isotropic phase transition temperature)=116° C.

IR (KBr, disc) $v_{max}$: 2918, 2848, 2110, 1508, 1468, 1271, 1072, 972, 891, 837 cm$^{-1}$

EXAMPLE 47

Preparation of trans-4-(trans-4-(4-trifluoromethylphenyloxymethyl)cyclohexyl)-1-(5-methoxypentyl)-4-silacyclohexane The general procedure of Example 39 was repeated using 4-trifluoromethylphenol and 4-(trans-4-bromomethylcyclohexyl)-4-phenyl-1-(5-methoxypentyl)-4-silacyclohexane, thereby obtaining the intended product.

EXAMPLE 48

Preparation of trans-4-(trans-4-(4-ethoxyphenyloxymethyl)-4-silacyclohexyl)-1-(4-pentenyl)cyclohexane The general procedure of Example 39 was repeated using 4-ethoxyphenol and trans-4-(4-bromomethyl-4-phenyl-4-silacyclohexyl)-1-(4-pentenyl)cyclohexane, thereby obtaining the intended product.

EXAMPLE 49

Preparation of trans-4-(trans-4-(4-difluoromethoxyphenyloxymethyl)-1-silacyclohexyl)-1-n-propyl-1-silacyclohexane The general procedure of Example 39 was repeated using 4-difluoromethoxyphenol and 4-bromomethyl-1-phenyl-1-silacyclohexyl-1-phenyl-1-n-propyl-1-silacyclohexane, thereby obtaining the intended product.

EXAMPLE 50

Preparation of trans-4-(trans-4-(4-cyano-3-fluorophenyloxymethyl)-1-silacyclohexyl)-1-n-pentyl-1-silacyclohexane The general procedure of Example 39 was repeated using 4-cyano-3-fluorophenol and 4-bromomethyl-1-phenyl-1-silacyclohexyl-1-phenyl-1-n-pentyl-1-silacyclohexyl, thereby obtaining the intended product.

EXAMPLE 51

Preparation of trans-4-(trans-4-(2,3-difluoro-4-n-propylphenyloxymethyl)cyclohexyl)-1-n-propyl-1-silacyclohexane The general procedure of Example 39 was repeated using 2,3-difluoro-4-n-propylphenol, thereby obtaining the intended product.

EXAMPLE 52

Preparation of trans-4-(trans-4-(4-chloro-2-fluorophenyloxymethyl)cyclohexyl)-1-n-propyl-1-silacyclohexane The general procedure of Example 39 was repeated using 4-chloro-2-fluorophenol, thereby obtaining the intended product.

EXAMPLE 53

Preparation of trans-4-(trans-4-(4-chloro-3-methylphenyloxymethyl)cyclohexyl)-1-n-propyl-1-silacyclohexane The general procedure of Example 39 was repeated using 4-chloro-3-methylphenol, thereby obtaining the intended product.

EXAMPLE 54

Preparation of trans-4-(trans-4-(3,4-difluorophenyloxymethyl)cyclohexyl)-1-(4-fluorobutyl)-1-silacyclohexane The general procedure of Example 39 was repeated using 3,4-difluorophenol and 4-(trans-4-bromomethylcyclohexyl)-1-phenyl-1-(4-fluorobutyl)-1-silacyclohexane, thereby obtaining the intended product.

EXAMPLE 55

Preparation of trans-4-(trans-4-(3,4,5-trifluorophenyloxymethyl)cyclohexyl)-1-(4-fluoropentyl)-1- silacyclohexane The general procedure of Example 39 was repeated using 3,4,5-trifluorophenol and 4-(trans-4-bromomethylcyclohexyl)-1-phenyl-1-(4-fluoropentyl)-1-silacyclohexane thereby obtaining the intended product.

EXAMPLE 56

Preparation of trans-4-(trans-4-(4-(2,2-difluorovinyl) phenyloxymethyl)cyclohexyl)-1-n-propyl-1-silacyclohexane The general procedure of Example 39 was repeated using 4-(2,2-difluorovinyl)phenol, thereby obtaining the intended product.

EXAMPLE 57

Preparation of trans-4-(trans-4-(3,5-difluoro-4-(2,2-trifluorovinyloxy)phenyloxymethyl)cyclohexyl)-1-n-pentyl-1-silacyclohexane The general procedure of Example 39 was repeated using 3,5-difluoro-4-(1,2,2-trifluorovinyloxy)phenol and 4-(trans-4-bromomethyloxycyclohexyl)-1-phenyl-1-n-pentyl-1-silacyclohexane, thereby obtaining the intended product.

EXAMPLE 58

Preparation of trans-4-(trans-4-(3,5-difluoro-4-(1,1,2,3,3,3-hexafluoropropoxy)phenyloxymethyl)cyclohexyl)-1-n-propyl-1-silacyclohexane The general procedure of Example 39 was repeated using 3,5-difluoro-4-(1,1,2,3,3,3-hexafluoropropoxy)phenol, thereby obtaining the intended product.

EXAMPLE 59

A mixture B consisting of 23 mole % of p-ethoxyphenyl trans-4-n-propylcyclohexanecarboxylate, 38 mole % of p-ethoxyphenyl trans-4-butylcyclohexanecarboxylate and 39 mole % of p-methoxyphenyl trans-4-n-pentylcyclohexanecarboxylate was prepared. The mixture B had the following properties.

$T_{NI}$ (nematic phase-isotropic phase transition temperature): 71° C.

$T_{CN}$ (crystal phase-nematic phase transition temperature): 15° C.

$\Delta\epsilon$ as (dielectric anisotropy): –1.3

A liquid crystal mixture consisting of 60 mole % of the mixture B and 40 mole % of trans-4-(trans-4-(2,3-difluoro-4-ethoxyphenyloxymethyl)cyclohexyl)-1-n-propyl-1-silacyclohexane obtained in Example 45 was prepared. This mixture exhibited a significant minus value and a nematic phase extended to a higher temperature range as shown below.

$T_{NI}$: 90° C.

$T_{CN}$: 20° C.

$\Delta\epsilon$: –4.6

When calculated from the above resets, the value of $\Delta\epsilon$ of the trans-4-(trans-4-(2,3-difluoro-4-ethoxyphenyloxymethyl)cyclohexyl)-1-n-propyl-1-silacyclohexane was –9.5, which is about 1.6 times greater than that of trans-4-(trans-4-(2,3-difluoro-4-ethoxyphenyloxymethyl)cyclohexyl)-1-n-propyl-1-cyclohexane which has a similar hydrocarbon skeletal structure.

EXAMPLE 60

A liquid crystal mixture consisting of 34 mole % of 2-(trans-4-n-pentylcyclohexyl)-1-(3,4-difluorophenyl) ethane, 15 mole % of 1,2-difluoro-4-[trans-4-(trans-4-n-propylcyclohexyl)cyclohexyl]benzene and 51 mole % of 2-[trans-4-(trans-4-n-propylcyclohexyl)cyclohexyl]-1-(3,4-difluorophenyl)ethane exhibited a nematic liquid crystal phase within a temperature range of from –17° C. to 63° C.

A liquid crystal mixture consisting of 80 mole % of the above mixture and 20 mole % of trans-4-(trans-4-(4-trifluoromethoxyphenyloxymethyl)cyclohexyl)-1-n-propyl-1-silacyclohexane obtained in Example 39 exhibited a nematic liquid crystal phase within an extended temperature range of –23° C. to 69° C.

As will be apparent from the above examples, the compounds of the general formula (II) of the invention are able to widely vary a dielectric anisotropy ranging from a great negative value to a great positive value by properly selecting the substituents of $L_1$, $L_2$ and X. Especially, with respect to the negative value of the dielectric anisotropy, its absolute value of the dielectric anisotropy is significantly greater than those absolute values attained by known liquid crystals substances having similar structures wherein the silicon atom is replaced by a carbon atom. This means that display devices utilizing the liquid crystal compounds of the invention can be driven at lower voltage.

What is claimed is:

1. A silacyclohexane compound selected from the group consisting of compounds of the following formulas (I) and (II)

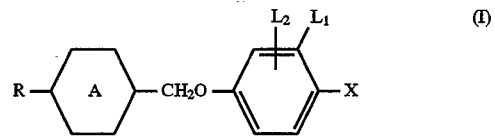

wherein R represents a linear alkyl group having from 1 to 10 carbon atoms, a branched alkyl group having from 8 to 8 carbon atoms, an alkoxyalkyl group having from 2 to 7 carbon atoms, a mono or difluoroalkyl group having from 1 to 10 carbon atoms, or an alkenyl group having from 2 to 8 carbon atom;

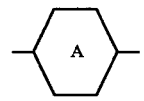

represents a trans-1-sila-1,4-cyclohexylene group or trans-4-sila-1,4-cyclohexylene group in which the silicon atom at the 1 or 4 position has a substituent of H, F, Cl or $CH_3$; $L_1$ and $L_2$ independently represent H, F, Cl or $CH_3$; and X represents a linear alkyl group having from 1 to 10 carbon atoms, a linear alkoxy group having from 1 to 10 carbon atoms, an alkoxyalkyl group having from 2 to 7 carbon atoms, a mono or difluoroalkyl group having from 1 to 10 carbon atoms, an alkenyl group having from 2 to 8 carbon atoms, CN, F, Cl, $CF_3$, $CF_2Cl$, $CHFCl$, $OCF_3$, $OCF_2Cl$, $OCHFCl$, $OCHF_2$, $(O)_YCY=CX_1X_2$ wherein is 0 or 1, Y and $X_1$ independently represent H, F or Cl, $X_2$ represents F or Cl, or $(O)_q(C_nF_mH_{2n-m})X_3$ wherein q is 0 or 1, n is 2,3 or 4; m is 0 or an integer of 1 to 2n, and $X_3$ represent H, F or Cl, and

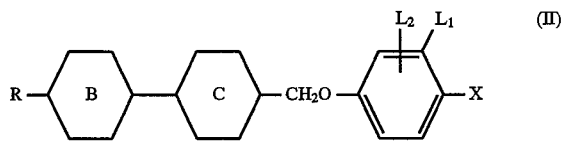

wherein R, $L_1$, $L_2$ and X are, respectively, as defined in the formula (I), and one of

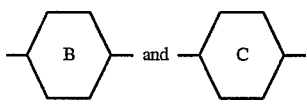

represents a trans-1-sila-1,4-cyclohexylene group or trans-4-sila-1,4-cyclohexylene group in which the silicon atom at the 1 or 4 position has a substituent of H, F, Cl or CH$_3$, and the other represents a trans-1,4-cyclohexylene group, or such a trans-1-sila-1,4-cyclohexylene group or trans-4-sila-1,4-cyclohexylene group as defined above.

2. A silacyclohexane compound according to claim 1, wherein said silacyclohexane compound is of the formula (I).

3. A silacyclohexane compound according to claim 2, wherein said silacyclohexane compound is of the following formula (Ia)

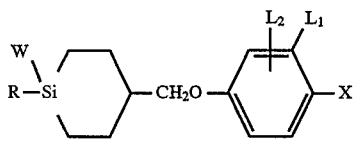

wherein W is H, F, Cl or CH$_3$.

4. A silacyclohexane compound according to claim 2, wherein said silacyclohexane compound is of the following formula (Ib)

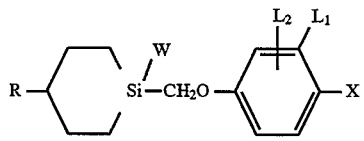

wherein W is H, F, Cl or CH$_3$.

5. A silacyclohexane compound according to claim 1, wherein said silacyclohexane compound is of the formula (II).

6. A silacyclohexane compound according to claim 5, wherein said silacyclohexane compound is of the following general formula (IIa)

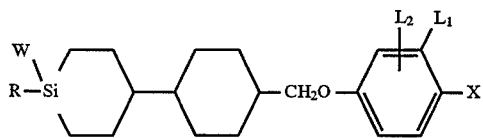

wherein W is H, F, Cl or CH$_3$.

7. A silacyclohexane compound according to claim 5, wherein said silacyclohexane compound is of the following general formula (IIb)

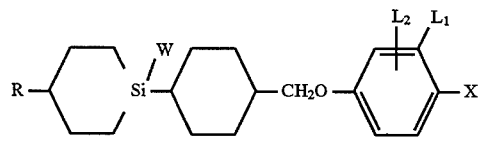

wherein W is H, F, Cl or CH$_3$.

8. A silacyclohexane compound according to claim 5, wherein said silacyclohexane compound is of the following general formula (IIc)

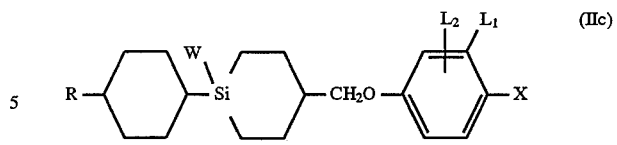

wherein W is H, F, Cl or CH$_3$.

9. A silacyclohexane compound according to claim 5, wherein said silacyclohexane compound is of the following general formula (IId)

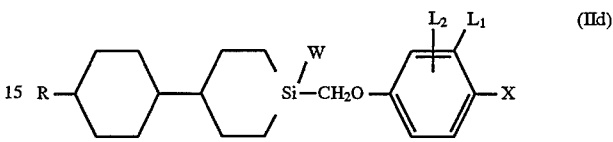

wherein W is H, F, Cl or CH$_3$.

10. A silacyclohexane compound according to claim 5, wherein said silacyclohexane compound is of the following general formula (IIe)

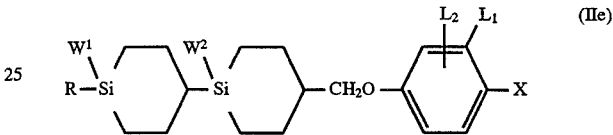

wherein $W_1$ and $W_2$ are, respectively, H, F, Cl or CH$_3$.

11. A silacyclohexane compound according to claim 5, wherein said silacyclohexane compound is of the following general formula (IIf)

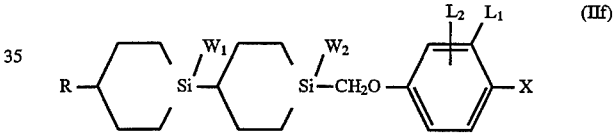

wherein $W_1$ and $W_2$ are, respectively, H, F, Cl or CH$_3$.

12. A silacyclohexane compound according to claim 5, wherein said silacyclohexane compound is of the following general formula (IIg)

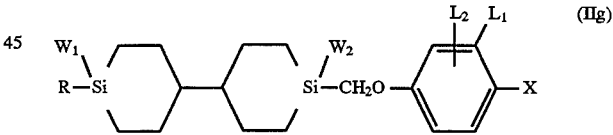

wherein $W_1$ and $W_2$ are, respectively, H, F, Cl or CH$_3$.

13. A process for preparing a silacyclohexane compound of the following general formula (I)

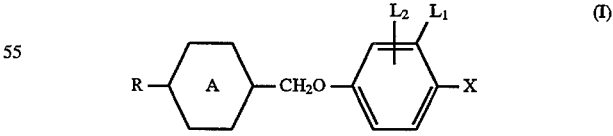

wherein R, $L_1$ $L_2$, X and

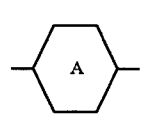

are, respectively, as defied in claim 1 the process comprising:

reacting an organometallic compound of the general formula, R—M wherein R is as defined in the formula (I) and M represents Li, MgP or ZnP wherein P is a halogen atom, with a compound of the following general formula (1)

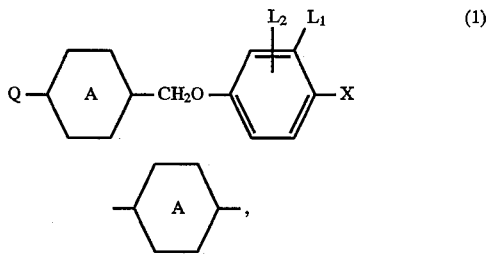

(1)

$L_1$, $L_2$ and X are, respectively, as defined in the formula (I), and Q represents a halogen atom, an alkoxy group having from 1 to 4 carbon atoms, a methanesulfonyloxy group, a benzenesulfonyl oxy group, a p-toluenesulfonyloxy group or a trifluoromethanesulfonyloxy group.

14. A process for preparing a silacyclohexane compound of the following general formula (I)

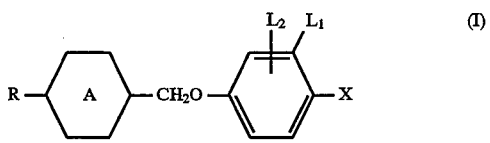

(I)

wherein R, $L_1$ $L_2$, X and

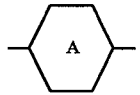

are, respectively, as defined in claim 1 the process comprising:

reacting a phenolic compound of the following general formula (2)

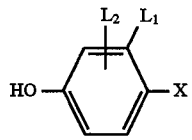

(2)

wherein $L_1$, $L_2$ and X are, respectively, as defined in the formula (I), with a compound of the following general formula (3)

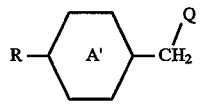

(3)

wherein

represents a trans-1-sila-1,4-cyclohexylene group or trans-4-sila-1,4-cyclohexylene group in which the silicon atom at the 1 or 4 position has a methyl group or Ar, wherein Ar represents phenyl tolyl, and Q represents a halogen atom, an alkoxy group having from 1 to 4 carbon atoms, a methanesulfonyloxy group, a benzenesulfonyloxy group, a p-toluenesulfonyloxy group or a trifluoromethanesulfonyloxy group, in the presence of a base to obtain a compound of the general formula (I) wherein

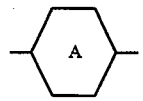

is a trans-1-sila-1,4-cyclohexylene group or trans-4-sila-4-cyclohexylene group whose silicon atom at the 1 or 4 position is substituted with methyl or Ar.

15. A process according to claim 14, wherein when a moiety of

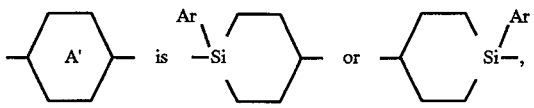

the compound obtained in claim 14 is further treated with iodine monochloride to convert the moiety to a moiety of the following formula

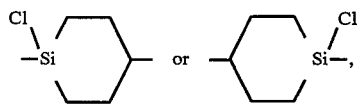

and then reduced
to obtain a moiety of the following formula

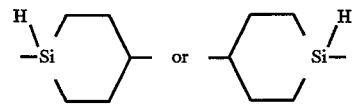

thereby obtaining a hydrosilacyclohexane compound.

16. A process for preparing a silacyclohexane compound of the general formula (II) defined in claim 1, the process comprising: reacting an organometallic compound of the general formula, R-M, wherein R is as defined in the formula (I) and M represents Li, MgP or ZnP wherein P is a halogen atom, with a compound of the following general formula (4)

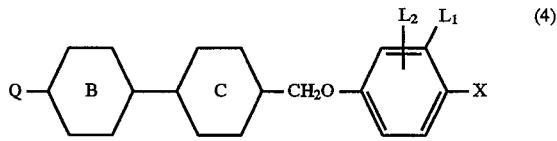

(4)

wherein

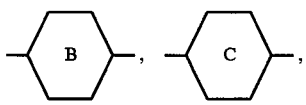

$L_1$, $L_2$ and X are, respectively, as defined in claim 1, and Q represents a halogen atom, a, alkoxy group having from 1 to 4 carbon atoms, a methanesulfonyloxy group, a benzenesulfonyloxy group, a p-toluenesulfonyloxy group or a trifluoromethanesulfonyloxy group.

17. A process for preparing a silacyclohexane compound of the general formula (II) defined in claim 1, the process comprising:

reacting an organometallic reagent of the following general formula

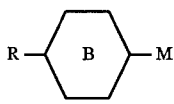    (5)

wherein R is as defined in claim 1 and M represents Li, MgP or ZnP wherein P is a halogen atom, with a compound of the following general formula (6)

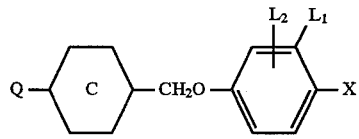    (6)

wherein

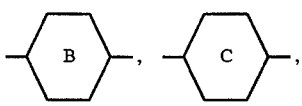

$L_1$, $L_2$ and X are, respectively, as defined in claim 1, and Q represent a halogen atom, an alkoxy group having from 1 to 4 carbon atoms, a methanesulfonyloxy group, a benzenesulfonyloxy group, a p-toluenesulfonyloxy group or a trifluoromethanesulfonyloxy group.

18. A process for preparing a silacyclohexane compound of the general formula (II) defined in claim 1, the process comprising:

reacting a phenolic compound of the following general formula (7)

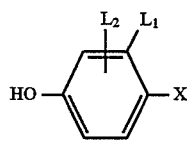    (7)

wherein $L_1$, $L_2$ and X are, respectively, as defined in claim 1, with a compound of re following general formula (8)

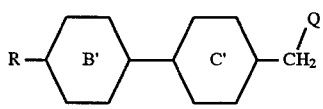    (8)

one of

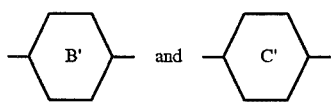

is a trans-1-sila-1,4-cyclohexylene group or trans-4-sila-1,4-cyclohexylene group wherein Si at the 1 or 4 position is substituted with a methyl group or Ar wherein Ar is phenyl or tolyl, and the other is a trans-1-sila-1,4-cyclohexylene group or trans-4-sila-1, 4-cyclohexylene group substituted as defined above, or a trans-1,4-cyclohexylene group, and Q represents a halogen atom, an alkoxy group having from 1 to 4 carbon atom, a methanesulfonyloxy group, a benzenesulfonyloxy group, a p-toluenesulfonyloxy group or a trifluoromethanesulfonyloxy group in the presence of a base to obtain a compound of the general formula (II) wherein the methyl group or Ar is attached to the silicon atom at the 1 or 4 position.

19. A process according to claim 18, wherein when at least one of

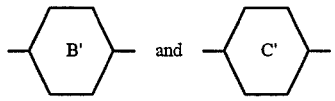

has an Ar substituent in the form of

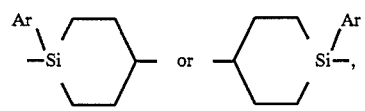

the at least one is de-silylated with iodine monochloride to provide a moiety of the following formula

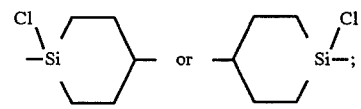

and reduced to obtain a moiety of the following formula

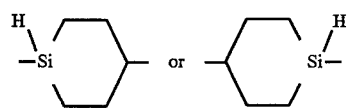

thereby obtaining a hydrosilacyclohexane compound of the general formula (II).

20. A liquid crystal composition comprising at least one silacyclohexane compound selected from the group consisting of compounds of the general formulas (I) and (II) defined in claim 1.

21. A liquid crystal composition according to claim 20, wherein said at least one silacyclohexane compound is present in an amount of from 1 to 50% by mole.

22. A liquid crystal composition according to claim 20, further comprising at least one compound selected from the group consisting of compounds of the following formulas

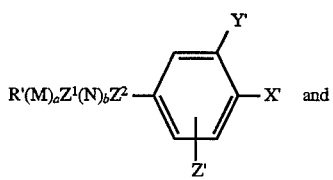

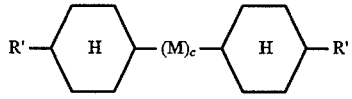

wherein each R' represents a linear alkyl group having from 1 to 10 carbon atoms, a branched alkyl group having from 3 to 8 carbon atoms, a mono or difluoroalkyl group having from 1 to 10 carbon atoms, an alkoxyalkyl group having from 2 to 7 carbon atoms or an alkenyl group having from 2 to 8 carbon atoms; X' represents a linear alkyl group having from 1 to 10 carbon atoms, a linear alkoxy group having from 1 to 10 carbon atoms, an alkoxyalkyl group having from 2 to 7 carbon atoms, CN, F, Cl, $CF_3$, $CF_2Cl$, $CHFCl$, $OCF_3$, $OCF_2Cl$, $OCHFCl$, $OCHF_2$; Y' and Z' independently represent H or F; M and N independently represent (1) an unsubstituted or substituted trans-1,4-cyclohexylene group, (2) a trans-1,4-cyclohexylene group wherein one $CH_2$ unit or two $CH_2$ units, which are not adjacent to each other, of the cyclohexane ring are replaced by O or S, (3) a 12,4-cyclohexenylene group, (4) an unsubstituted or substituted 1,4-phenylene group and (5) a 1,4-phenylene group in which one or two CH units of the phenylene group are replaced by nitrogen atom, a and b are, respectively, 0, 1 or 2 provided that a+b=1, 2 or 3, and c is 0, 1 or 2; and $Z^1$ and $Z^2$ are, respectively, —$CH_2CH_2$—, —CH=CH—, —C≡C—, —$CO_2$—, —OCO—, —$CH_2O$—, —$OCH_2$— or single bond.

23. A liquid crystal display device comprising the composition defined in claim 20.

\* \* \* \* \*